(12) United States Patent
Bowers, III et al.

(10) Patent No.: US 10,416,126 B2
(45) Date of Patent: Sep. 17, 2019

(54) MACHINE FAULT PREDICTION BASED ON ANALYSIS OF PERIODIC INFORMATION IN A SIGNAL

(71) Applicant: Computational Systems, Inc., Knoxville, TN (US)

(72) Inventors: Stewart V. Bowers, III, Knoxville, TN (US); Robert D. Skeirik, Knoxville, TN (US)

(73) Assignee: Computational Systems, Inc., Knoxville, TN (US)

( * ) Notice: Subject to any disclaimer, the term of this patent is extended or adjusted under 35 U.S.C. 154(b) by 127 days.

(21) Appl. No.: 15/697,911

(22) Filed: Sep. 7, 2017

(65) Prior Publication Data

US 2018/0011065 A1 Jan. 11, 2018

Related U.S. Application Data

(63) Continuation-in-part of application No. 14/316,883, filed on Jun. 27, 2014, now Pat. No. 9,791,422.
(Continued)

(51) Int. Cl.
*G01N 29/50* (2006.01)
*G01H 1/00* (2006.01)
(Continued)

(52) U.S. Cl.
CPC .............. *G01N 29/50* (2013.01); *G01H 1/00* (2013.01); *G01H 1/06* (2013.01); *G01H 1/08* (2013.01);
(Continued)

(58) Field of Classification Search
CPC .... G01N 29/50; G01N 29/14; G01N 29/4427; G01N 29/4454; G01N 29/46;
(Continued)

(56) References Cited

U.S. PATENT DOCUMENTS

| 8,174,402 | B2* | 5/2012 | Bouse | G05B 19/4065 |
| | | | | 340/635 |
| 10,133,257 | B2* | 11/2018 | Hedin | G01H 1/003 |
| 2016/0146700 | A1* | 5/2016 | Hedin | G01H 1/003 |
| | | | | 702/56 |

OTHER PUBLICATIONS

Flowserve Corporation; IPS Wireless Auto Vibration Analysis Eight Peaks;Services and Solutions Asset Management and Optimization; FSG-115a (E/A4) Oct. 2014; Copyright 2014 Flowserve Corporation; 2 pages.

* cited by examiner

*Primary Examiner* — Bryan Bui
(74) *Attorney, Agent, or Firm* — Luedeka Neely Group, P.C.

(57) ABSTRACT

A "periodic signal parameter" (PSP) indicates periodic patterns in an autocorrelated vibration waveform and potential faults in a monitored machine. The PSP is calculated based on statistical measures derived from an autocorrelation waveform and characteristics of an associated vibration waveform. The PSP provides an indication of periodicity and a generalization of potential fault, whereas characteristics of the associated waveform indicate severity. A "periodic information plot" (PIP) is derived from a vibration signal processed using two analysis techniques to produce two X-Y graphs of the signal data that share a common X-axis. The PIP is created by correlating the Y-values on the two graphs based on the corresponding X-value. The amplitudes of Y-values in the PIP is derived from the two source graphs by multiplication, taking a ratio, averaging, or keeping the maximum value.

36 Claims, 21 Drawing Sheets

Related U.S. Application Data

(60) Provisional application No. 62/410,935, filed on Oct. 21, 2016, provisional application No. 61/842,035, filed on Jul. 2, 2013.

(51) Int. Cl.
| | |
|---|---|
| *G01H 1/06* | (2006.01) |
| *G01H 1/08* | (2006.01) |
| *G01N 29/44* | (2006.01) |
| *G01N 29/46* | (2006.01) |
| *G01N 29/14* | (2006.01) |
| *G01N 29/48* | (2006.01) |
| *G01M 13/045* | (2019.01) |

(52) U.S. Cl.
CPC .......... *G01M 13/045* (2013.01); *G01N 29/14* (2013.01); *G01N 29/4427* (2013.01); *G01N 29/4454* (2013.01); *G01N 29/46* (2013.01); *G01N 29/48* (2013.01)

(58) Field of Classification Search
CPC ............ G01N 29/48; G01H 1/00; G01H 1/06; G01H 1/08; G01M 13/045
See application file for complete search history.

PSP = 0.05

PSP = 0.10

PSP = 0.115

PSP = 0.147

PSP = 0.52

MACHINE FAULT PREDICTION BASED ON ANALYSIS OF PERIODIC INFORMATION IN A SIGNAL

RELATED APPLICATIONS

This application claims priority as a continuation-in-part of U.S. Non-Provisional patent application Ser. No. 14/316,883 filed Jun. 27, 2014, titled "Analysis of Periodic Information in a Signal," which claims priority to U.S. provisional patent application Ser. No. 61/842,035 filed Jul. 2, 2013, titled "Periodic Signal Parameter."

FIELD

This invention relates to analysis of signals. More particularly, this invention relates to methods for extracting and applying periodic information from a vibration waveform or other signal containing periodic information.

BACKGROUND

By some estimates, up to half of all mechanical failures in process plants are induced by process conditions. Therefore, providing feedback to an operator that the process machines are being operated in a non-optimal configuration provides a way for the operator to avoid harmful operating states, thereby substantially extending mean time between failures (MTBF) or mean time between repairs (MTBR) on production assets.

Vibration analysis is a well proven technology for detecting faults in rotating machinery. The process of determining the severity and specifics of a fault can be very involved. Part of the analysis process involves determining whether periodic signals are present. While maintenance personnel are concerned with detailed analyses of faults, operations personnel only want to know if a problem exists. Providing a few fault-related parameters to the operator can be sufficient in accomplishing this task. Fault-related parameters can be related to amplitudes of energy from particular vibration frequencies (bandwidth), signal processing techniques such as PeakVue™, and the presence of periodic and non-periodic signals. Parameters calculated from bandwidth and signal processing techniques are well defined. However, a parameter indicating the presence of periodic and non-periodic signals has not been defined.

Further, the ability to detect mechanical faults in industrial rotating equipment is a task requiring skilled analytical personnel with years of training and experience. The technician performing the machine diagnosis must be skilled in the techniques and technologies used to analyze the machine. A typical vibration spectrum used for such analysis will contain 1,600 data points, but may contain upwards of 12,800 points. Practically, only a handful of these data values are significant for the diagnosis of the machine. It typically takes several weeks of training followed by 18-24 months of practice for the technician to be skilled in identifying the handful of peaks that are required for the diagnosis. Developing and maintaining employees who are qualified to serve as technicians is a major concern in industry, because an individual plant may only have one such individual on staff. This dynamic is further exacerbated by the trend towards having a central diagnostician be responsible for analyzing data collected across multiple plant sites—further reducing the availability of redundant skills within the organization. Therefore, new technologies and data plots are required that will reduce training requirements and simplify the identification of pertinent data points within the larger data set.

Additionally, a vibration analyst needs tools to help differentiate between non-periodic and periodic information in a vibration signal. For example, analysis tools are needed to extract a low-amplitude periodic signal (e.g. 10 g signal) indicating a bearing fault out of a large non-periodic signal (e.g. 70 g signal) caused by under lubrication. This is a common situation, in which a lack of adequate lubrication inevitably leads to an actual mechanical defect in the bearing. Catching it early is very important to extended machine life.

A separate but equally concerning dynamic is that a single individual is being asked to analyze the data from multiple sites. In such situations, even an experienced analyst requires additional tools that pre-select and extract pertinent information from the larger data set, thereby significantly reducing the amount of data that must be screened by the analyst, streamlining the diagnostic process, and increasing both the efficiency and accuracy of the diagnosis.

Further, the management of large data sets presents a continual challenge for any individual required to interface with the data. This includes transmission, storage and retrieval of collected data.

Transmission. Due to large data sets required for traditional vibration analysis, transmission of vibration data can be very challenging with smaller or restricted data pipes. One example is transmission via a wireless link, where specific bandwidth allocations exist. Another example is the application of a prescribed wireless protocol, such as HART® or WirelessHART®, where each data packet has a pre-defined size that is far too small to accommodate a traditional vibration measurement.

Storage. Drastic reductions in the cost of computer memory have lead many disciplines, including vibration analysis, to develop tools that are extensively data centric. However, with the advent of cloud-based data storage, the cost of memory is increasing again, forcing users to prioritize which information is stored or retained.

Retrieval. Relational databases developed to support business systems have proven to be less than ideal for vibration analysis. This is due to the large file size of vibration readings. As the size of a relational database grows, the retrieval time to access and display a specific data set increases significantly. Given that a typical vibration spectrum may be composed of over 12,800 data points, and the raw vibration waveform associated with this spectrum may have over 30,000 data points, and that there may be tens of thousands of such measurements in a typical process facility, it is easy to see how the size of a vibration database could quickly become inappropriate for the application of a relational database.

For these reasons, there is a critical need to develop new techniques to reduce training requirements, improve the efficiency of an analyst without compromising accuracy, enable data transmission across limited data pipes, reduce vibration traffic across larger data pipes, reduce memory requirements to store diagnostic data, and enable users to access and display stored data with high responsiveness and faster retrieval times.

SUMMARY

Periodic Signal Parameter

The autocorrelation coefficient function is a mathematical process that can be used to determine how much of the energy in a waveform is periodic. The pattern of the periodic peaks—or lack thereof—can be very helpful in identifying fault types. Recognizing these patterns and how to apply them requires an experienced analyst. Preferred embodiments of the present invention calculate a value that is representative of general periodic patterns that signify potential faults. This value, referred to herein as a "periodic signal parameter" (PSP), is calculated based on statistical measures derived from an autocorrelation waveform along with characteristics of the associated vibration waveform. While the PSP derived from the autocorrelation function produces an indication of periodicity and a generalization of potential fault, characteristics of the associated vibration waveform afford a measure of severity. The combination of these two identities provides further indication as to potential problems associated with machines on the plant floor. Beyond focusing the efforts of a vibration analyst, this provides a significant advantage for a machine operator on the plant floor who may have little-to-no vibration analysis experience.

The process of calculating the PSP begins with calculating the autocorrelation function of a vibration waveform. Once this is accomplished, several statistical calculations are performed. In a preferred embodiment, these statistical calculations include the maximum absolute waveform peak, standard deviation of the waveform, maximum absolute peak after the first 3% of the waveform, crest factor of both the waveform and positive waveform values, and a sorted mean of positive waveform peak values. The sorted mean is preferably calculated from a subset of values, in this case the larger set is the positive waveform peak values. The sorted subset preferably comprises all peak values from the positive waveform, excluding outliers. The outliers are peak values that exceed a statistically defined standard deviation about the mean. Therefore, the sorted mean is the mean value of the sorted positive waveform peak subset.

Once the PSP is calculated, the peak-to-peak amplitude of the initial vibration waveform (which in a preferred embodiment that would be the peak amplitude in the PeakVue™ waveform) is evaluated. Various aspects of the PeakVue™ process are described in U.S. Pat. No. 5,895,857 (Robinson et al.), U.S. Pat. No. 6,192,325 (Piety et al.), U.S. Pat. No. 6,549,869 (Piety et al.), U.S. Pat. No. 6,889,553 (Robinson et al.), U.S. Pat. No. 7,561,200 (Garvey et al.), U.S. Pat. No. 7,424,403 (Robinson et al.), U.S. Pat. No. 8,174,402 (Reeves et al.), 2014/0039833 (White et al.), and 2012/0041695 (Baldwin et al.), the entire contents of which are incorporated herein by reference. However other techniques could be applied to extract pertinent information from the vibration signal to generate the initial vibration waveform, including but not limited to Enveloping, High Frequency Enveloping, Spectral Emitted Energy, Spike Energy™, and Shock Pulse™. If the peak-to-peak amplitude of the associated vibration waveform exceeds predefined alarm limits, indication of particular faults are triggered based on the PSP value.

Because the autocorrelation of a waveform is normalized to ±1, the maximum standard deviation of the waveform is 1. Therefore, the base value of the PSP ranges from 0 to 1. Mathematical operations can be performed on the base value to achieve a desired scaling. An example would be to multiply the base value by 10 to achieve a PSP range from 0 to 10. Additionally, taking the square root of the PSP base value accentuates variations in the lower end of the scale, which can then be multiplied by 10 to achieve a PSP range from 0 to 10. As discussed in more detail hereinafter, the PSP is calculated based on the value of the standard deviation of the autocorrelated waveform plus contributions centered on empirical observations from the other calculated statistical parameters mentioned above. Examples of autocorrelated waveforms along with the associated PSP values are provided in the detailed description.

The PSP may apply to autocorrelated waveforms derived from filtered and unfiltered acceleration, velocity or displacement waveforms as well as processed waveforms. Two examples of processed waveforms are results of the PeakVue™ signal processing and demodulation techniques.

Periodic Information Plot

As discussed above, the autocorrelation coefficient function is a mathematical process that indicates whether there is periodicity in a signal. When viewing an autocorrelation waveform, periodic signals are typically evident in the data. However, it is not easy to distinguish the exact frequency or amplitude of these periodic signals from the autocorrelation waveform. By taking a Fast Fourier Transform (FFT) of the autocorrelation waveform, distinct frequency values are evident. By comparing the autocorrelation spectrum to the standard spectrum, the true amplitude of each signal at these frequencies can be obtained.

Preferred embodiments described herein provide methods for analyzing and displaying data to reveal periodicity in a signal. The embodiments include processing the raw signal using two different sets of analysis techniques, thereby producing two X-Y graphic representations of the signal data that share a common X-axis. A third graph is created by correlating the Y-values on the first two graphs based on the corresponding X-value. The amplitude of each Y-value can be derived from the two source graphs using a variety of techniques, including multiplication, taking a ratio, averaging, or keeping the maximum value. The resulting synthesized graph, also referred to herein as a Periodic Information Plot (PIP), accentuates signal components that are pertinent to a given diagnosis while eliminating other undesired signal components. This provides for visualizing the data in a way that simplifies the recognition and quantification of desired characteristics present in the raw signal. Also, the absence of periodic signal components is diagnostically significant and may be equally important to the maintenance decisions performed in a plant. The diagnosis may be accomplished either by a human or a computerized expert system. For a human analyst, the technique reduces training requirements while bringing increased efficiency and accuracy. With a computerized expert system, the technique provides new methods for diagnostic software to recognize significant patterns contained in the original signal.

Thus, the analysis process is made easier by providing the analyst with a plot showing only the periodic signals present in the data. While the same periodic information is present in the original spectrum generated from the original data, it is often difficult to recognize the periodic information because the level of noise and other non-periodic signals is similar to or greater than the amplitude of the periodic information.

For example, Table 1 below compares a traditional vibration spectrum (FIG. 9) with its associated PIP (FIG. 12).

TABLE 1

Comparison of Traditional Vibration Spectrum and PIP

| Data Plot Type | Data Points | Transmit Time | Data Storage | Retrieval Time | Analysis Time |
|---|---|---|---|---|---|
| Traditional Vibration Spectrum (See FIG. 9) | 1,600 | 100% | 100% | 100% | 100% |
| Periodic Information Plot (See FIG. 12) | 11 | <2% | <2% | <50% | <50% |

Based on Table 1, it is apparent that embodiments of the invention significantly reduce the number of data points to be processed, which reduces network transmission time and required bandwidth. The reduction in data points also reduces the amount of space needed for data storage, as well as the time needed to retrieve data from storage devices. Accordingly, embodiments described herein significantly increase the efficiency and speed of the measurement system depicted in FIGS. 1A and 1B as compared to prior vibration analysis systems.

Furthermore, eliminating random or insignificant peaks from the data set significantly improves data quality as an input into an expert diagnostic system. This not only decreases processing time, but also improves the diagnostic result and streamlines the interpretation.

Predicting Faults Based on Periodic Signal Parameter (PSP)

An estimate of the condition of a roller element bearing can be predicted by combining the PSP and the maximum peak amplitude of the associated waveform from which an autocorrelation was performed, and optionally speed. For example, the combination of these parameters can indicate the severity of a bearing fault and/or any lubrication issues that may be present. Similarly, the condition of teeth in a gearbox and the health of roller element bearings in the gearbox can be determined.

In general, a PSP greater than 0.1 indicates that a periodic signal is present. Any periodicity that is not a harmonic of running speed (referred to herein as nonsynchronous periodicity) is typically associated with a bearing fault, such as inner or outer race faults along with rolling element and cage faults. The severity of a bearing fault may be determined based on the peak amplitude of the associated PeakVue waveform. This severity is proportional to the fault levels determined in part by the turning speed of the bearing. When a gearbox is being monitored, any synchronous periodicity is related to the health of the gear teeth. The severity of gear teeth faults is related to the PeakVue waveform peak amplitude and is proportional to fault levels dictated by the associated gear speed. When large peak amplitude values are present in the PeakVue waveform and PSP≤0.1, then lubrication issues are suspected in roller element bearings and/or gearboxes.

Preferred embodiments described herein present bearing fault and lubrication information in an easy to understand format. In one embodiment depicted in FIG. 18, the information is presented as one diagnostic gauge that indicates the presence and severity of a bearing fault and another diagnostic gauge that indicates the presence and severity of a lubrication problem. For gearbox applications, a third gauge may indicate the condition of the gear teeth in a gearbox. Other embodiments show bearing condition information in other graphical formats, such as test tube displays, red-yellow-green light displays, and many others. Thus, the invention is not limited to any particular format for presenting the severity information.

By combining the results indicated by the diagnostic gauges with the Periodic Information Plot (PIP), an analyst can easily visualize the condition of the machinery being monitored. Based on this simplified initial visualization, the analyst can predict faults to be acted upon or investigated if desired. Thus, the PIP plays an important role in calculations and is an integral part of the simplified analysis summary.

Some embodiments described herein provide an apparatus for acquiring and analyzing periodic information in vibration associated with a machine. The apparatus of these embodiments includes a vibration sensor, a data collector, and a periodic information processor. The vibration sensor is securely attached to the machine in a location that provides a solid transmission path from a source of vibration within the machine to the vibration sensor. The data collector is configured to receive and condition the vibration signal from the vibration sensor. The data collector includes an analog-to-digital converter for converting the vibration signal to digital vibration data, and memory for buffering the digital vibration data.

The periodic information processor is configured to execute operational instructions for processing the digital vibration data. When executed, these operational instructions:

generate an original waveform based on the digital vibration data;
perform an autocorrelation function on the original waveform to generate an autocorrelation waveform;
perform a Fast Fourier Transform on the original waveform to generate an original spectrum;
perform a Fast Fourier Transform on the autocorrelation waveform to generate an autocorrelation spectrum;
compile a first list of amplitude peaks from the original spectrum;
compile a second list of amplitude peaks from the autocorrelation spectrum;
match autocorrelation amplitude peaks in the second list with original amplitude peaks in the first list;
add to a peak list each original amplitude peak that matches an autocorrelation amplitude peak;
as original amplitude peaks are added to the peak list, determine a total amount of peak energy associated with the original amplitude peaks in the peak list; and
after the total amount of peak energy associated with the original amplitude peaks in the peak list exceeds a predetermined threshold, generate a periodic information plot comprising the original amplitude peaks in the peak list.

In some embodiments, the periodic information processor generates the periodic information plot having at least 80% fewer data points than the original spectrum.

In some embodiments, the predetermined threshold comprises a percent energy value, and wherein the periodic information processor is configured to execute operational instructions for calculating the percent energy value according to $$\% \text{ Energy of Original} = \text{Total energy of original spectrum} \times \% \text{ Periodic Energy}$$

wherein $$\% \text{ Periodic Energy} = \sqrt{\text{MaxPeak}(\text{after3\%ofwaveform})}$$

wherein MaxPeak (after 3% of waveform) comprises a maximum absolute peak in the autocorrelation waveform occurring outside the first 3% of the autocorrelation waveform.

In some embodiments, the original waveform is a Peak-Vue waveform.

In some embodiments, the periodic information processor is configured to execute operational instructions to arrange the amplitude peaks in the first and second lists in order of descending amplitude, such that a largest amplitude peak is first and a smallest amplitude peak is last.

In some embodiments, the periodic information processor is configured to execute operational instructions to classify the amplitude peaks as synchronous peaks and nonsynchronous peaks, to assign one or more first display colors to the synchronous peaks in the periodic information plot, and to assign one or more second display colors to the nonsynchronous peaks in the periodic information plot, wherein the first display colors are different from the second display colors.

In some embodiments, the periodic information processor is configured to execute operational instructions to separate amplitude peaks that are synchronous peaks into multiple families and to assign a different display color to each family of synchronous peaks in the periodic information plot.

In some embodiments, the apparatus includes a data communication network to which the periodic information processor is connected and through which the periodic information plot is communicated. An analyst computer is connected to the data communication network for receiving and displaying the periodic information plot for viewing by an analyst.

In some embodiments, the periodic information processor determines a match between an autocorrelation amplitude peak from the second list and an original amplitude peak from the first list when

|original peak frequency−autocorrelation peak frequency|≤n×ΔFrequency, where the original peak frequency is a frequency value of the original amplitude peak from the first list, the autocorrelation peak frequency is a frequency value of the autocorrelation amplitude peak from the second list, and n is an integer value. The value of ΔFrequency is determined according to:

$$\Delta Frequency = \frac{F\max \text{ of original spectrum}}{LOR \text{ of original spectrum}}.$$

In some embodiments, the data collector comprises a digital data recorder or a vibration data collector.

In some embodiments, the data collector includes a low-pass anti-aliasing filter.

In some embodiments, the periodic information processor is a component of the data collector.

In some embodiments, the periodic information processor is a component of an analyst computer that is in communication with the data collector via a communication network.

In some embodiments, the periodic information processor is configured to execute operational instructions that:
generate an original waveform based on the digital vibration data;
perform a Fast Fourier Transform on the original waveform to generate an original spectrum having amplitude values $Y_{VS}(n)$, where n=1 to N, and N is a number of frequency values;
perform an autocorrelation function on the original waveform to generate an autocorrelation waveform;
perform a Fast Fourier Transform on the autocorrelation waveform to generate an autocorrelation spectrum having amplitude values $Y_{AS}(n)$, where n=1 to N, where N is the number frequency values;
combine adjacent pairs of amplitude values $Y_{VS}(2n)$ and $Y_{VS}(2n-1)$ in the original spectrum, according to $$Y_{MCVS}(n) = \sqrt{(Y_{VS}(2n-1))^2 + (Y_{VS}(2n))^2}; \text{ and}$$

combine the original spectrum and the autocorrelation spectrum to generate a periodic information plot having amplitude values $Y_{PIP1}(n)$, according to $$Y_{PIP1}(n) = Y_{MCVS}(n) \times Y_{AS}(n), \text{ where } n=1 \text{ to } N.$$

Inclusion of the amplitude values $Y_{PIP1}(n)$ in the periodic information plot accentuates signal components that are pertinent to a diagnosis by the analyst while eliminating undesired non-periodic signal components, thereby improving visualization of pertinent signal components.

In some embodiments, the periodic information processor is configured to execute operational instructions to generate a periodic information plot having amplitude values $Y_{PIP3}(n)$, according to If $Y_{PIP1}(n) > Y_{THR}$, $Y_{PIP3}(n) = Y_{PIP1}(n)$ If $Y_{PIP1}(n) \leq Y_{THR}$, $Y_{PIP3}(n) = 0$ where n=1 to N, and $Y_{THR}$ is a predetermined threshold value.

In some embodiments, the periodic information processor is configured to execute operational instructions to perform an inverse Fast Fourier Transform on the periodic information plot to generate an information waveform.

In some embodiments, the periodic information processor is configured to execute operational instructions to derive a circular information plot from the information waveform.

In some embodiments, the periodic information processor executes operational instructions that:
generate an original waveform based on the digital vibration data;
perform a Fast Fourier Transform on the original waveform to generate an original spectrum having amplitude values $Y_{VS}(n)$, where n=1 to M, and M is a number of frequency values;
perform an autocorrelation function on the original waveform to generate an autocorrelation waveform;
perform a Fast Fourier Transform on the autocorrelation waveform to generate an autocorrelation spectrum having amplitude values $Y_{AS}(n)$, where n=1 to N, where N is the number of frequency values;
combine adjacent pairs of amplitude values $Y_{VS}(2n)$ and $Y_{VS}(2n-1)$ in the original spectrum, according to $$Y_{MCVS}(n) = \sqrt{(Y_{VS}(2n-1))^2 + (Y_{VS}(2n))^2}; \text{ and}$$

generate a periodic information plot having amplitude values $Y_{PIP2}(n)$, according to If $Y_{AS}(n) > Y_{THR}$, $Y_{PIP2}(n) = Y_{MCVS}(n)$ If $Y_{AS}(n) \leq Y_{THR}$, $Y_{PIP2}(n) = 0$, where n=1 to N, and $Y_{THR}$ is a predetermined threshold value.

Inclusion of only the amplitude values $Y_{PIP2}(n)$ in the periodic information plot accentuates signal components that are pertinent to a diagnosis by the analyst, while eliminating undesired non-periodic signal components, thereby improving visualization of pertinent signal components.

In some embodiments, the periodic information processor executes operational instructions that:
  generate an original waveform based on the digital vibration data;
  perform a Fast Fourier Transform on the digital vibration data to generate an original spectrum having amplitude values $Y_{VS}(n)$, where n=1 to N, where N is a number of frequency values;
  combine adjacent pairs of amplitude values $Y_{VS}(2n)$ and $Y_{VS}(2n-1)$ in the original spectrum, according to $$Y_{MCVS}(n) = \sqrt{(Y_{VS}(2n-1))^2 + (Y_{VS}(2n))^2};$$

perform an autocorrelation function on the original waveform to generate an autocorrelation waveform;
  perform a Fast Fourier Transform on the autocorrelation waveform to generate an autocorrelation spectrum having amplitude values $Y_{AS}(n)$, where n=1 to N, where N is the number of frequency values; and
  combine the original spectrum and the autocorrelation spectrum to generate a periodicity map having coordinate values $X_{PM}(n)$ and $Y_{PM}(n)$ determined according to $$X_{PM}(n) = Y_{MCVS}(n)$$

$$Y_{PM}(n) = Y_{AS}(n)$$

for n=1 to N.

In some embodiments, the periodic information processor executes operational instructions that:
  generate an original waveform based on the digital vibration data;
  perform an autocorrelation function on the original waveform to generate an autocorrelation waveform;
  perform a Fast Fourier Transform on the autocorrelation waveform to generate an autocorrelation spectrum having amplitude values $Y_{AS}(n)$, where n=1 to N;
  generate a non-periodic information plot having amplitude values $Y_{NPIP}(n)$, according to If $Y_{AS}(n) < Y_{THR}$, $Y_{NPIP}(n) = Y_{AS}(n)$ If $Y_{AS}(n) \geq Y_{THR}$, $Y_{NPIP}(n) = 0$, where n=1 to N, and $Y_{THR}$ is a predetermined threshold value.

Inclusion of only the amplitude values $Y_{NPIP}(n)$ in the non-periodic information plot accentuates signal components that are pertinent to a diagnosis by the analyst, while eliminating undesired non-periodic signal components, thereby improving visualization of pertinent signal components.

In some embodiments, the periodic information processor executes operational instructions that:
  generate an original waveform based on the digital vibration data;
  determine a maximum peak amplitude of the original waveform;
  perform an autocorrelation function on the original waveform to generate an autocorrelation waveform;
  determine a periodic signal parameter value based at least in part on the autocorrelation waveform, where the periodic signal parameter value comprises a single real number indicative of a level of periodic information in the original waveform;
  calculate or receive a fault limit level; and
  calculate one or more severity values based on the maximum peak amplitude and the fault limit level.

In some embodiments, the original waveform is a Peak-Vue waveform.

In some embodiments, if the periodic signal parameter value is greater than 0.1 and the machine speed is unknown, the periodic information processor calculates a Bearing Fault Severity (BFS) value according to:

$$BFS = \text{Normalized Severity} \times \% \text{ Periodic Energy,}$$

where $$\text{Normalized Severity} = \frac{\text{MaxPeak}}{2 \times \text{Fault Limit}} \times x$$

and $$\% \text{ Periodic Energy} = \sqrt{\text{MaxPeak(after first 3\%)}}.$$

In some embodiments, if the periodic signal parameter value is greater than 0.1 and machine speed is known, the periodic information processor calculates a Bearing Fault Severity (BFS) value according to:

$$BFS = \text{Normalized severity} \times$$

$$\left[\left(\frac{(\text{energy of the located nonsynchronous peaks})^2}{(\text{total energy of the associated } PeakVue \text{ spectrum})^2}\right)\right]$$

where $$\text{Normalized Severity} = \frac{\text{MaxPeak}}{2 \times \text{Fault Limit}} \times x.$$

In some embodiments, the periodic information processor is configured to execute operational instructions to calculate an alert limit level based on the turning speed. If the periodic signal parameter value is less than 0.1 and the maximum peak amplitude of the original waveform is greater than the alert limit level, the periodic information processor calculates a Lubrication Severity (LS) value according to:

$$LS = \frac{\text{MaxPeak}}{2 \times \text{Fault Limit}} \times x \times \% \text{ NPE,}$$

wherein Percent Non-Periodic Energy (% NPE) is a function of Percent Periodic Energy (% Periodic Energy), such as depicted in FIG. 19. Percent Periodic Energy is calculated from the autocorrelation waveform according to:
  % Periodic Energy = $\sqrt{\text{MaxPeak(afterfirst3\%)}}$.

In some embodiments, the periodic information processor is configured to execute operational instructions to calculate a Gearbox Fault Severity (GFS) value according to:

$$GFS = \text{Normalized Severity} \times$$

$$\left[\left(\frac{(\text{energy of the located nonsynchronous peaks})^2}{(\text{total energy of the associated } PeakVue \text{ spectrum})^2}\right)\right]$$

where $$\text{Normalized Severity} = \text{General Severity} \times x$$

and $$\text{General Severity} = \text{MaxPeak}/(2 \times \text{Fault Limit})$$

and x is a normalization factor.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1A:
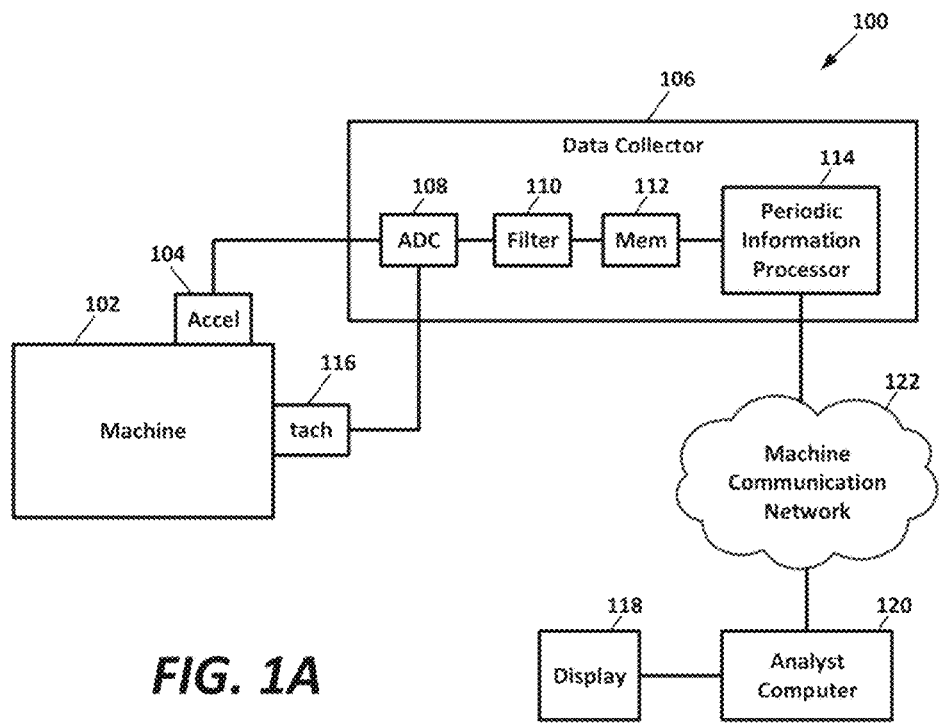
FIGS. 1A and 1B depict functional block diagrams of a system for deriving and analyzing periodic information in a signal according to preferred embodiments of the invention.
Figure 1B:
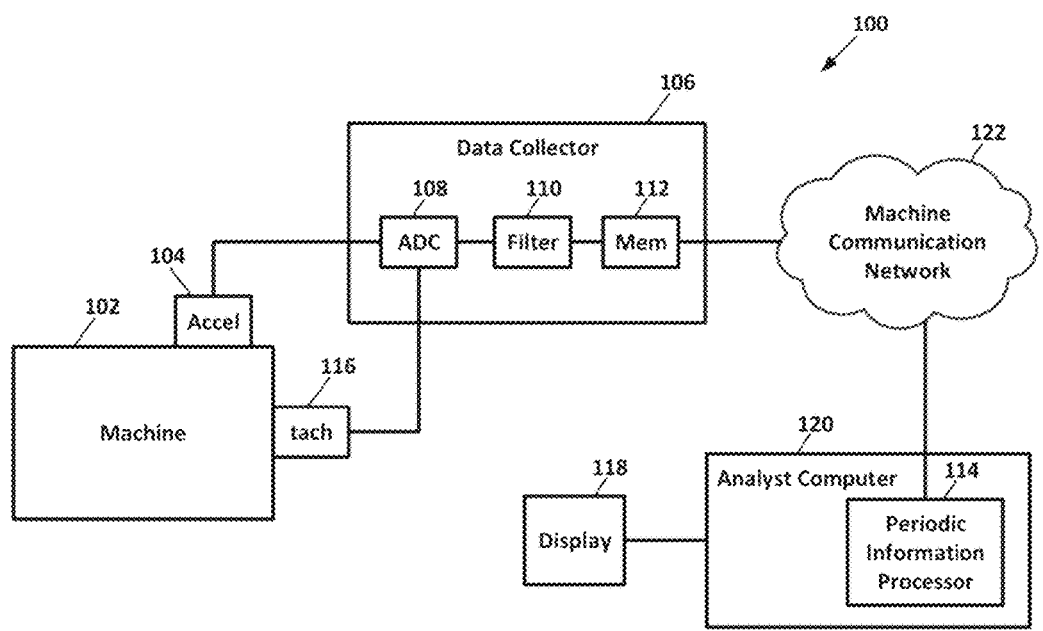

FIGS. 1A and 1B depict exemplary systems 100 for deriving and analyzing periodic information in a vibration signal. In the embodiment of FIG. 1A, a sensor 104, such as an accelerometer, is attached to a machine 102 to monitor its vibration. Although an accelerometer is depicted in the exemplary embodiment of FIG. 1A, it should be appreciated that other types of sensors could be used, such as a velocity sensor, a displacement probe, an ultrasonic sensor, or a pressure sensor. The sensor 104 generates a vibration signal (or other type of signal for a sensor other than an accelerometer) that contains periodic information. For repeatable and best results, it is preferable to place each sensor 104 such that there is a solid path of transition from the signal source (e.g. a bearing) to the mounting location of the sensor. The mounting of the sensor 104 should also be performed to ensure that the signal is sensed with as minimal distortion as possible. Preferred embodiments include one or more tachometers 116 for measuring the rotational speed of one or more rotating components of the machine 102. The vibration and tachometer signals are provided to a data collector 106 preferably comprising an analog-to-digital converter (ADC) 108 for sampling the vibration and tachometer signals, an optional low-pass anti-aliasing filter 110 (or other combination of low-pass and high-pass filters), and buffer memory 112. For example, the data collector 106 may be a digital data recorder, a handheld vibration data collector, or a permanently or temporarily mounted monitoring device. The vibration signal data is communicated to a periodic information processor 114 that performs the information processing tasks described herein. In the embodiment of FIG. 1A, the periodic information processor 114 is a component of the data collector 106. In this embodiment, the periodic information processor 114 communicates processed data via a machine data network 122, which may be a HART™ or WirelessHART™ network, an Ethernet network, or the Internet. An analyst computer 120 receives the processed data via the network 122 for display on a display device 118.

In an alternative embodiment depicted in FIG. 1B, the periodic information processor 114 is a component of the analyst computer 120. This embodiment may be preferable for situations in which data transmission and storage are not a major concern, so that the entire data set can be transferred via the network 122 to the analyst computer 120 or other remote processing device for post-processing using the same algorithms and techniques.

With regard to sensor placement for bearing and gear diagnosis, the sensor 104 is typically mounted orthogonal to the shaft. It is preferably mounted on a rigid and massive piece of metal that is near the source of the signal (i.e. bearing or gear). The large mass of metal on which the sensor is mounted helps prevent resonances entering the signal due to the surface of the machine as opposed to what is happening internal to the machine. The sensor 104 should be mounted so as to minimize loss of signal integrity during transmission. This requires a rigid connection—typically by stud mounting the sensor 104. In some circumstances, such as where the mounting surface of the machine is rough or covered with many layers of paint, the surface will need to be sanded.

Periodic Signal Parameter

Figure 2:
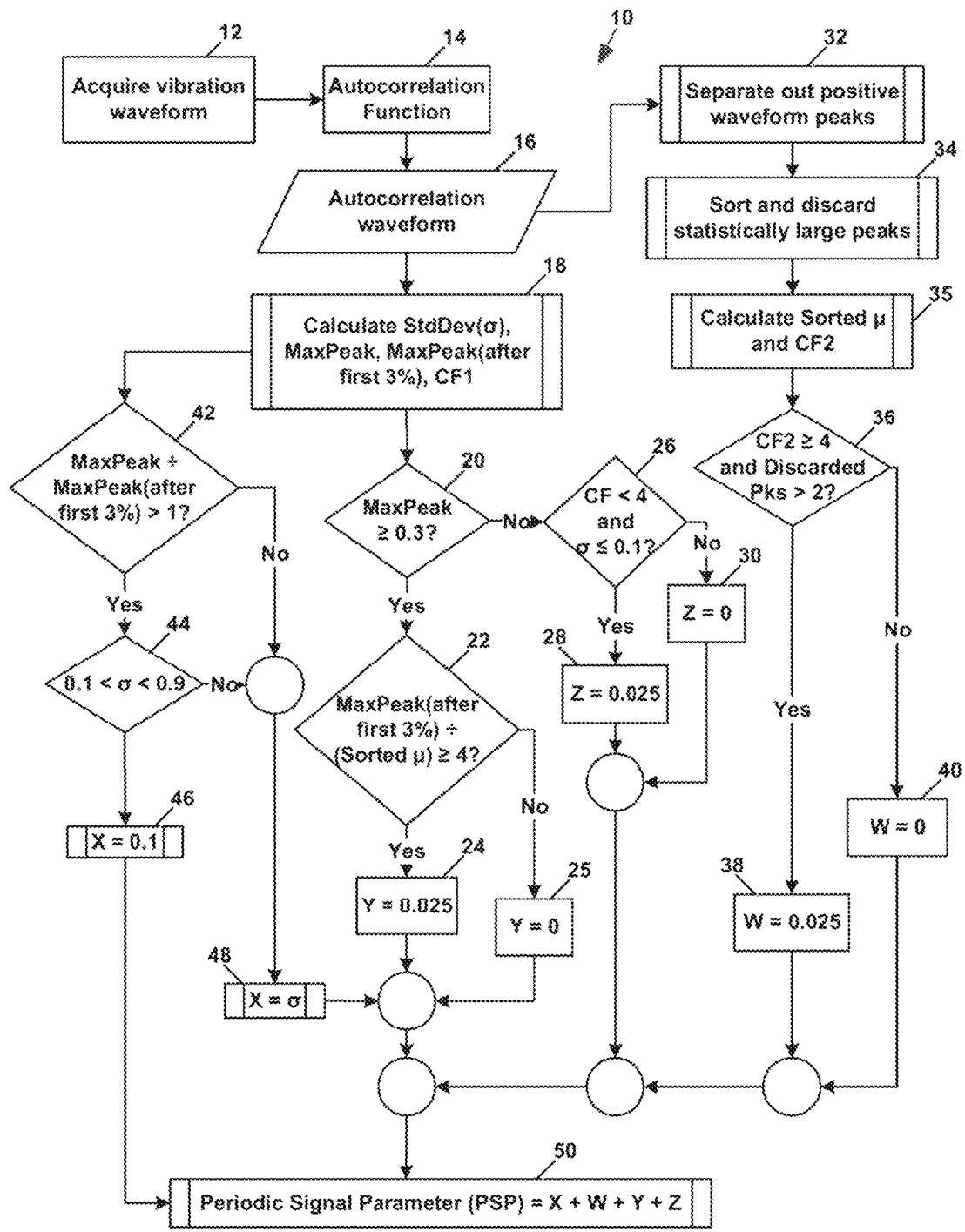
FIG. 2 depicts a flowchart of a method for determining a periodic signal parameter according to a preferred embodiment of the invention.

FIG. 2 depicts a flowchart of a method for calculating a periodic signal parameter (PSP) according to a preferred embodiment of the invention. A time-domain vibration waveform is measured, such as using the accelerometer 104 or other sensor attached to the machine 102 being monitored (step 12). An autocorrelation function is performed on the vibration waveform to determine how much of the energy in the waveform is periodic (step 14). In a preferred embodiment, the autocorrelation function cross-correlates the vibration signal with itself to find repeating patterns within the waveform. The autocorrelation function outputs an autocorrelation waveform 16, examples of which are depicted in FIGS. 3-7. Several statistical characteristics of the autocorrelation waveform are calculated, including the standard deviation (σ), the maximum absolute peak amplitude in the waveform (MaxPeak), the maximum absolute peak after the first 3% of the waveform (MaxPeak (after first 3%)), and the crest factor (CF1) (step 18). The positive waveform peaks are sorted out (step 32), any of those peaks that are statistically too large are discarded (step 34), and the mean amplitude (sorted μ) and the crest factor (CF2) of the remaining peaks are calculated (step 35). Methods for sorting and discarding peaks that are statistically too large are described hereinafter.

If MaxPeak is greater than or equal to 0.3 (step 20) and $$\frac{\text{MaxPeak(after first 3\%)}}{\text{sorted } \mu} \geq 4 \text{(step 22), then } Y = 0.025 \text{(step 24)}.$$

If MaxPeak is greater than or equal to 0.3 (step 20) and $$\frac{\text{MaxPeak(after first 3\%)}}{\text{sorted } \mu} < 4$$

(step 22), then Y=0 (step 25).

If MaxPeak is less than 0.3 (step 20) and CF1 less than 4 and σ is less than or equal to 0.1 (step 26), then Z=0.025 (step 28). If MaxPeak is less than 0.3 (step 20) and CF1 is not less than 4 or σ is greater than 0.1 (step 26), then Z=0 (step 30).

If CF2 is greater than or equal to 4 and the number of discarded peaks is greater than 2 (step 36), then W=0.025 (step 38). If CF2 is less than 4 or the number of discarded peaks is not greater than 2 (step 36), then W=0 (step 40).

If $$\frac{\text{MaxPeak}}{\text{MaxPeak(after first 3\%)}} > 1$$

(step 42) and σ is between 0.1 and 0.9 (step 44), then X=0.1 (step 46). If $$\frac{\text{MaxPeak}}{\text{MaxPeak(after first 3\%)}} \leq 1$$

(step 42) or σ is not between 0.1 and 0.9 (step 44), then X=σ (step 48).

The PSP is the sum of the values of X, W, Y and Z (step 50).

Figure 3:
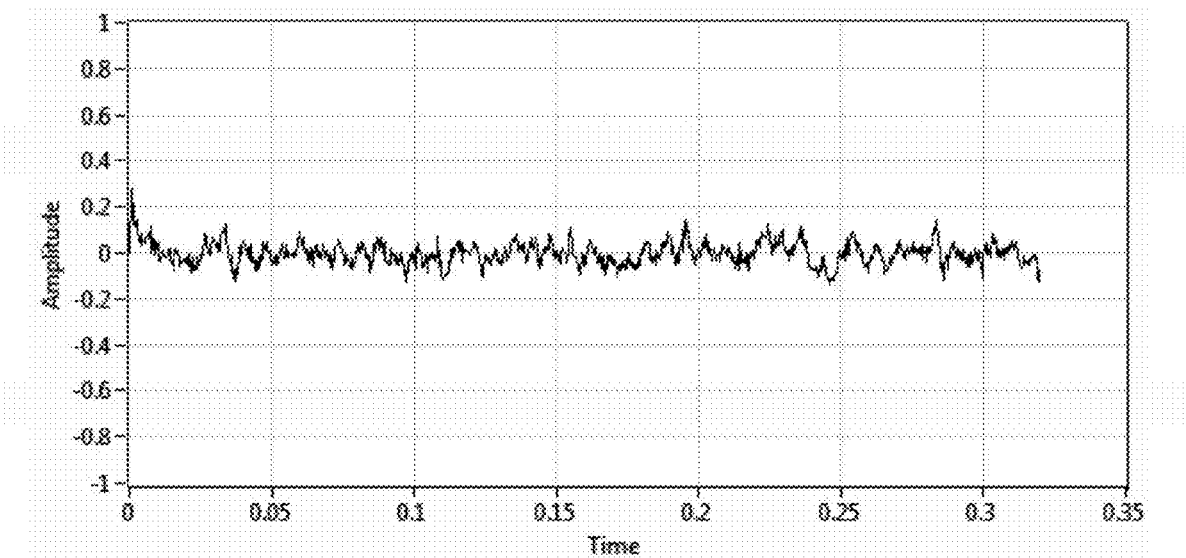
FIGS. 3-7 depict exemplary autocorrelated vibration waveforms for various values of a periodic signal parameter.
Figure 4:
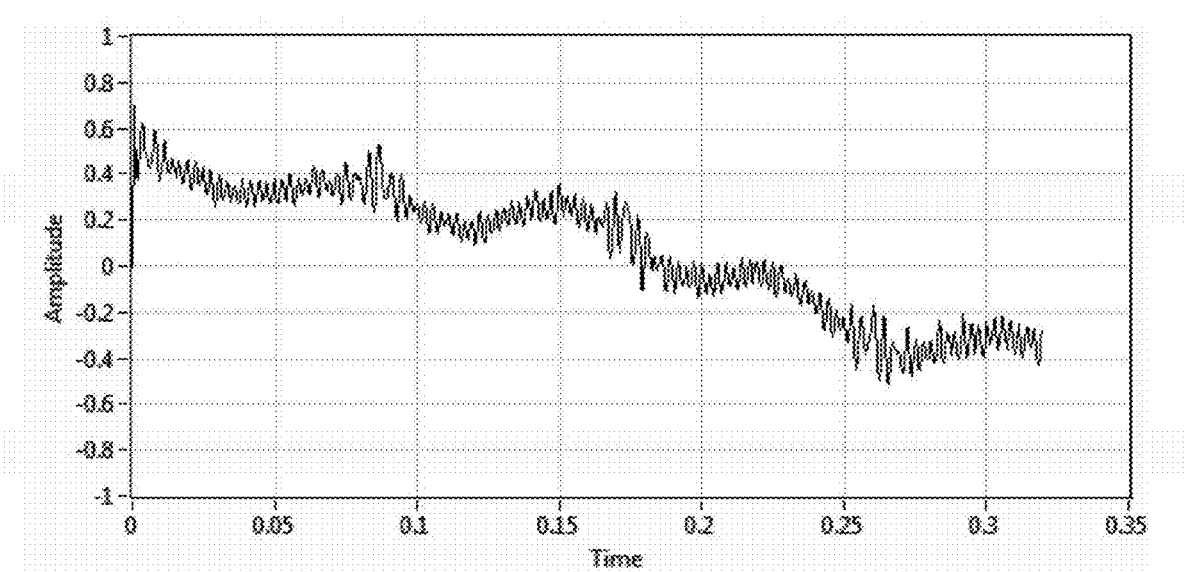
Figure 5:
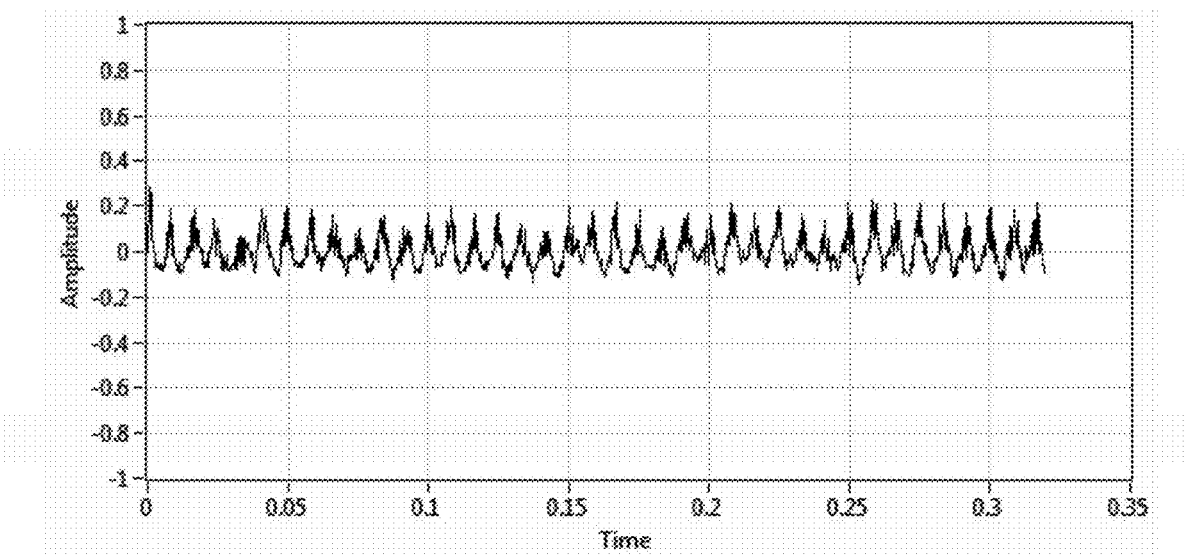
Figure 6:
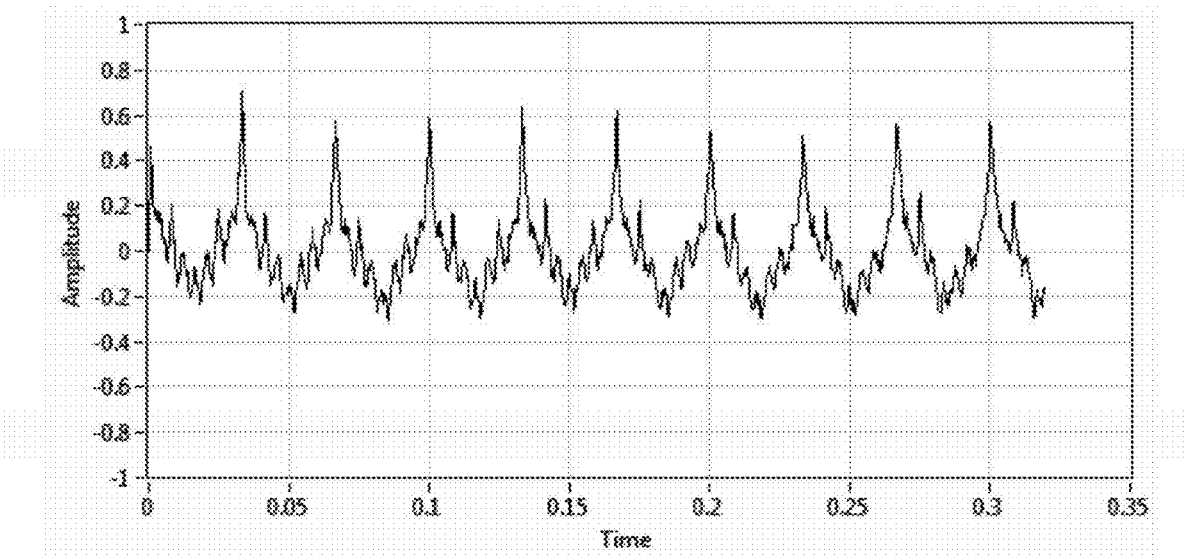
Figure 7:
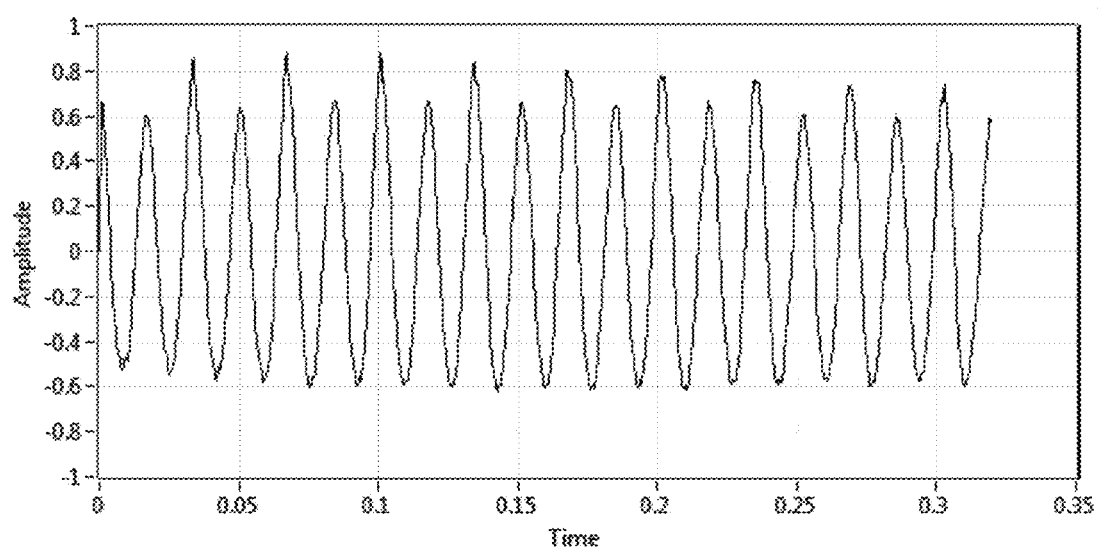

In general, smaller PSP values are indicative of more non-periodic signals and less distinctive frequencies, while larger PSP values are symptomatic of more periodic signals relating to large single frequencies. As shown in FIG. 3, PSP values of less than a first threshold, such as 0.1, indicate that the vibration waveform is mostly non-periodic. As shown in FIG. 4, the algorithm for the PSP assigns a value of 0.1 to signals having low amplitude, higher frequency data. This data may also prove to be bad data. As shown in FIG. 5, PSP values between first and second thresholds, such as between about 0.10 and 0.14, indicate that distinct frequencies are present but there is still a significant amount of non-periodic content. As shown in FIG. 6, PSP values greater than the second threshold, such as greater than about 0.14, indicate very distinctive frequencies that are important to analysis, such as vane pass or ball pass frequencies, along with small amplitude signals indicative of lower frequencies, such as RPM or cage along with their harmonics. As shown in FIG. 7, PSP values greater than a third threshold, such as greater than 0.5 and above, indicate large dominant single frequencies in the spectrum taken from the vibration waveform. The closer the PSP value is to 1.0, the waveform has more periodic signal components and less non-periodic content.

Following are some advantages of generating a PSP.

The PSP provides a single number indicative of the periodic content in a waveform.

Statistical values are calculated from the autocorrelated waveform and one or more of these values are combined to produce the PSP.

Indication of bad data or non-periodic signals is provided.

Information about periodicity can be extracted from a large data set and broadcast via a small bandwidth protocol such as HART®, WirelessHART®, and other similar protocols.

The PSP value may be applied specifically to PeakVue™ data in order to distinguish between periodic and non-periodic faults, such as lubrication, cavitation, bearing, gear and rotor faults.

The PSP value can be used in conjunction with other information to generate an indication of machine condition (i.e. nature of mechanical fault, severity of the fault). The other information may include:

the original waveform;

processed versions of the waveform;

information obtained from the original vibration waveform (i.e. peak value, crest factor, kurtosis, skewness);

information obtained from a processed version of the original waveform (i.e. PeakVue™ processed, rectified, or demodulated waveform); and/or one or more rule sets.

An example is illustrated in Table 2 below, where derived values representing PSP output and Stress Wave Analysis output (for example, maximum peak in the PeakVue™ waveform or another derivative of PeakVue™ type analysis or another form of stress wave analysis) are used to distinguish between different types of faults. In the majority of cases, the severity of the defect increases as the level of PeakVue™ impacting increases. Although the example below refers to a Stress Wave value, other embodiments may use other vibration waveform information indicative of an impacting or other fault condition.

TABLE 2

| | PSP and Stress Wave Analyses Outputs | |
|---|---|---|
| Periodic [right]<br>Stress Wave [below] | PSP - Low<br>(PSP < PSP threshold) | PSP - High<br>(PSP > PSP threshold) |
| PeakVue ™ or other stress wave analysis - Low (Stress Wave value < Stress Wave threshold) | No fault indication: no action called for based on this finding | Early stage periodic fault released defect: look for early indication of one of the periodic fault types such as those listed below |

TABLE 2-continued

PSP and Stress Wave Analyses Outputs

| Periodic [right]<br>Stress Wave [below] | PSP - Low<br>(PSP < PSP threshold) | PSP - High<br>(PSP > PSP threshold) |
|---|---|---|
| PeakVue ™ or other stress wave analysis - High (Stress wave value > Stress Wave threshold) | Non-periodic fault:<br>look for further or confirming evidence of inadequate lubrication or leak or contact friction or pump cavitation | Periodic fault:<br>look for rolling element bearing defect or gear defect or other source of repetitive periodic mechanical impacting - use frequency information and other information to distinguish among multiple possible causes |

A further embodiment of the present invention employs a programmable central processing unit, such as the processor 114, programmed with program logic to assist a user with an interpretation of waveform information. The program logic compares the Periodic Signal Parameter and Stress Wave analysis information with expected or historical or empirically-derived experiential values to discern a relative ranking from low to high. Then discrete or graduated outputs, such as those portrayed in Table 2 above, are employed to select logically arrayed observations, findings, and recommendations. In addition to evaluating PSP and Stress Wave Analysis information, program logic sometimes prompts a user to supply additional information or obtains additional information from another source such as from a knowledge base, to enable the logic to distinguish between two or more possible logical results. For example, program logic that returns a high PSP and a high Stress Wave Analysis finding may select a rolling element defect finding rather than other possible findings within that category because a similarity is calculated when program logic compares a periodic frequency finding and a bearing fault frequency for a machine component identified in a knowledge base.

Another technique to differentiate between lubrication and pump cavitation is to look at the trend of the impacting as indicated by Stress Wave analysis. If it increases slowly, then insufficient lubrication should be suspected. If it increases suddenly on a pump, then it is likely pump cavitation. If combined with logic or inputs on a control system, then the logic could look for process configuration changes that occurred at the same time as the increase in impacting—along with a low PSP—to confirm pump cavitation. In some embodiments, the system suggests to the operator what action caused the cavitation, so that the operator can remove the cause and stop the machine from wearing excessively and failing prematurely.

Periodic Information Plot

A preferred embodiment of the invention creates a new type of vibration spectrum, referred to herein as a Periodic Information Plot (PIP). The PIP provides the user an easily viewed summary of the predominate periodic peaks from the originating spectrum, which would be a PeakVue spectrum in a preferred embodiment.

PIP Generation—First Embodiment

Figure 8:
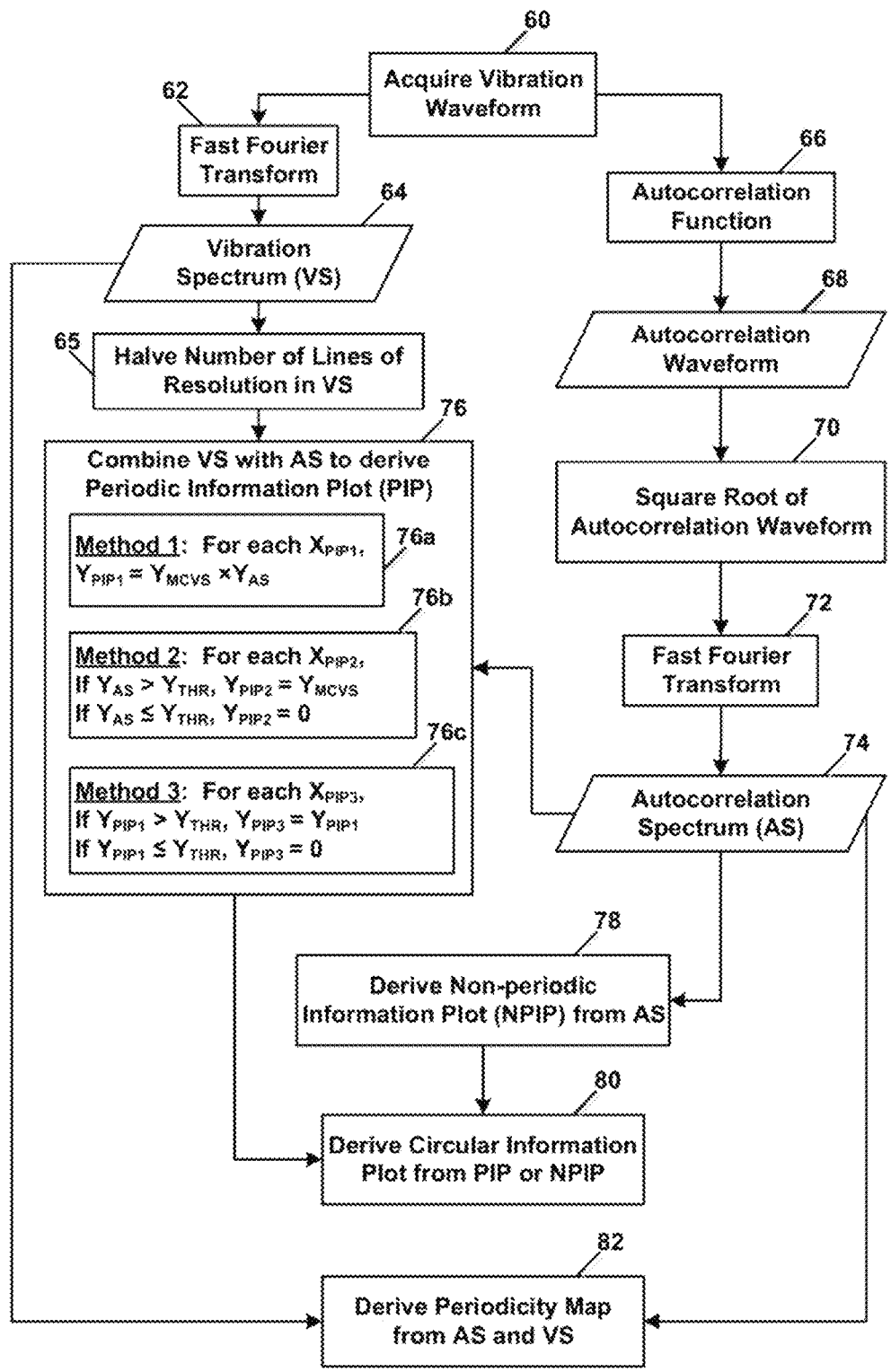
FIG. 8 depicts a flowchart of a method for generating a periodic information plot according to a first embodiment of the invention.

In a first embodiment, a signal is collected from plant equipment (e.g. rotating or reciprocating equipment) and is processed using two different sets of analysis techniques as depicted in FIG. 8.

Figure 9:
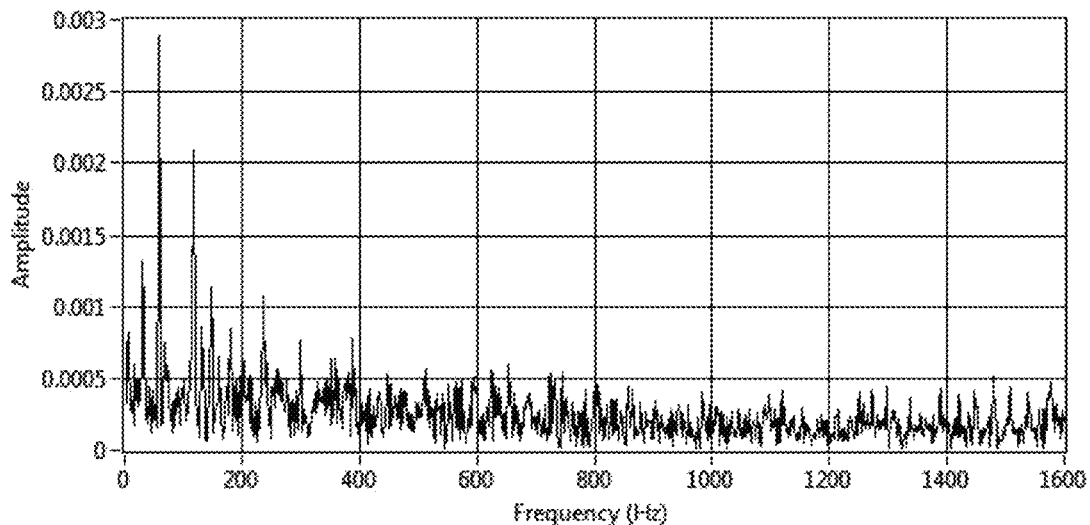
FIG. 9 depicts an exemplary standard vibration spectrum.

First, a waveform is acquired (step 60 of FIG. 8), such as a vibration waveform acquired using the system depicted in FIG. 1A. If employing a high-pass filter and peak-hold decimation to an oversampled waveform to capture impacting information (such as using the PeakVue™ process), this may be a calculated waveform. An FFT of the waveform is taken (step 62), resulting in a vibration spectrum (VS) 64 with frequency on the X-axis and amplitude on the Y-axis, an example of which is shown in FIG. 9.

The waveform from step 60 is also autocorrelated (step 66) to generate a waveform referred to herein as the autocorrelation waveform 68, having time on the X-axis and the correlation factor on the Y-axis. The autocorrelation process accentuates periodic components of the original waveform, while diminishing the presence of random events in the original signal. As a result of the autocorrelation calculations, the autocorrelation waveform 68 has half the x-axis (time) values as that of the original vibration waveform 60. Therefore, the timespan of the autocorrelation waveform 68 will be half of that of the original vibration waveform 60. An optional step (70) takes the square root of the autocorrelation waveform (Y-axis values) to provide better differentiation between lower amplitude values.

Figure 10:
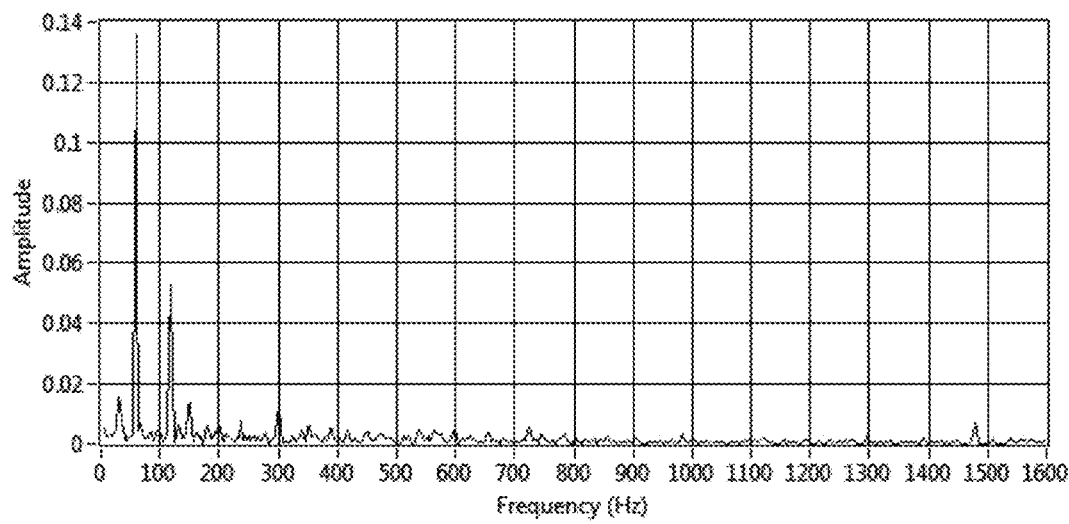
FIG. 10 depicts an exemplary autocorrelated vibration spectrum derived from the spectrum depicted in FIG. 9.

An FFT of the autocorrelation waveform 68 is taken (step 72), resulting in an autocorrelation spectrum (AS) 74. Since random events have largely been removed from the autocorrelation waveform 68, the remaining signal in the autocorrelation spectrum 74 is strongly related to periodic events. As shown in FIG. 10, the autocorrelation spectrum 74 has frequency on the X-axis and amplitude related to the correlation factor on the Y-axis. Because the autocorrelation waveform's duration is half that of the vibration waveform 60, the associated autocorrelation spectrum 74 has half the lines of resolution compared to the vibration spectrum 64.

In the first embodiment, the vibration spectrum 64 and the autocorrelation spectrum 74 are processed to derive a graph referred to herein as the Periodic Information Plot (PIP) (step 76). Several methods for processing the vibration spectrum 64 and the autocorrelation spectrum 74 may be used according to the first embodiment, three of which are described below.

Because the vibration spectrum is twice the resolution of the autocorrelation spectrum, a point-to-point comparison for values on the x-axis (frequency) between the two spectra is not possible. However, a point-to-point comparison can be made by mathematically combining the amplitude values of two x-axis values in the vibration spectrum (step 65) for each associated x-axis value in the autocorrelation spectrum. Each $X_{AS}(n)$ value of the autocorrelation spectrum (where n=1 ... N, and N is the number of lines of resolution for the autocorrelation spectrum) is mapped to the $X_{VS}(2n)$ value on the vibration spectrum. The mathematically combined x-axis value is defined such that $X_{MCVS}(n)=X_{VS}(2n)$. The mathematically combined amplitude values $Y_{VS}(2n)$ and $Y_{VS}(2n-1)$ (herein termed $Y_{MCVS}(n)$) associated with the $X_{MCVS}(n)$ value from the vibration spectrum are calculated from the amplitudes of both the $X_{VS}(2n)$ and $X_{VS}(2n-1)$ frequencies from the x-axis. The calculation for deriving the mathematically combined amplitude value associated with the $X_{MCVS}(n)$ value from the vibration spectrum is:

$$Y_{MCVS}(n)=\sqrt{(Y_{VS}(2n-1))^2+(Y_{VS}(2n))^2}, \qquad \text{Eq. (0)}$$

where n=1 ... N and N is the number of lines of resolution found in the autocorrelation spectrum.

Figure 11:
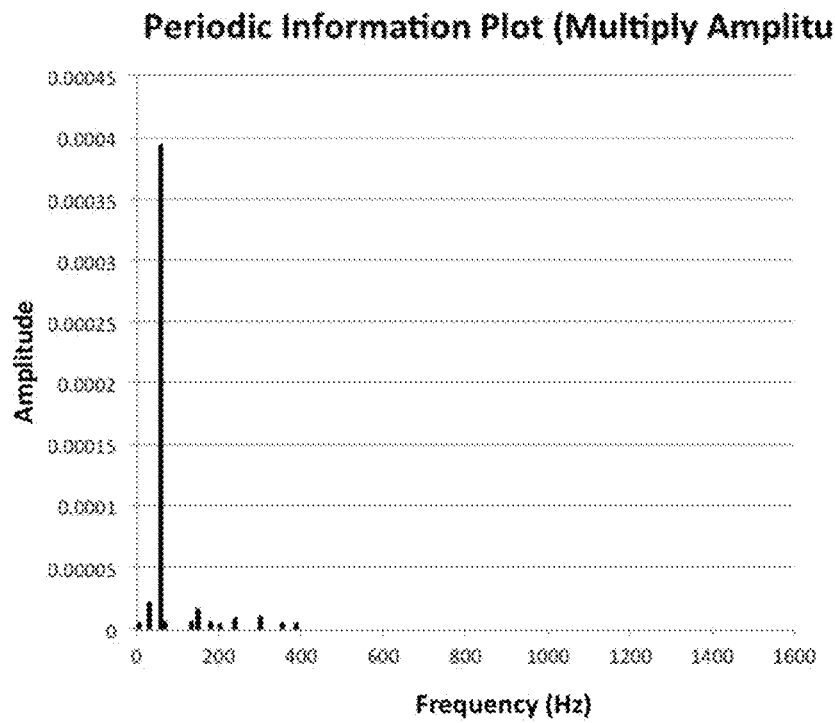
FIGS. 11-17 depict periodic information plots generated based on the spectrum depicted in FIG. 9 according to preferred embodiments of the invention.

In a first method (step 76a), for each X-value in the PIP ($X_{PIP1}$), the Y-value in the PIP ($Y_{PIP1}$) is determined by multiplying the mathematically combined Y-value in the vibration spectrum ($Y_{MCVS}$) by the corresponding Y-value in the autocorrelation spectrum ($Y_{AS}$), according to:

$$Y_{PIP1}(n)=Y_{MCVS}(n) \times Y_{AS}(n) \qquad \text{Eq. (1)}$$

for n=1 to N, where N is the number of X-values (frequency values) in the autocorrelation spectrum. Since amplitudes of periodic signals in the autocorrelation spectrum are higher than the amplitudes of random signals, the multiplication process will accentuate the periodic peaks while decreasing non-periodic peaks. An example of a PIP formed by the first method is depicted in FIG. 11. In all of the examples depicted herein, N=1600.

In a second method (step 76b), for each X-value in the PIP ($X_{PIP2}$), the Y-value in the PIP ($Y_{PIP2}$) is determined by comparing the corresponding Y-value in the autocorrelation spectrum ($Y_{AS}$) to a predetermined threshold value ($Y_{THR}$). For each autocorrelation spectrum amplitude greater than this threshold value, the associated amplitude for PIP ($Y_{PIP2}(n)$) will be set to the corresponding mathematically combined value from the vibration spectrum ($Y_{MCVS}(n)$). $Y_{AS}$ values above the predetermined threshold indicate data that is largely periodic. Thus, the $Y_{PIP2}$ values are determined according to:

$$\text{If } Y_{AS}(n) > Y_{THR}, Y_{PIP2}(n) = Y_{MCVS}(n) \qquad \text{Eq. (2a)}$$

$$\text{If } Y_{AS}(n) \leq Y_{THR}, Y_{PIP2}(n) = 0 \text{ (or some other default level)} \qquad \text{Eq. (2b)}$$

for n=1 to N.

Figure 12:
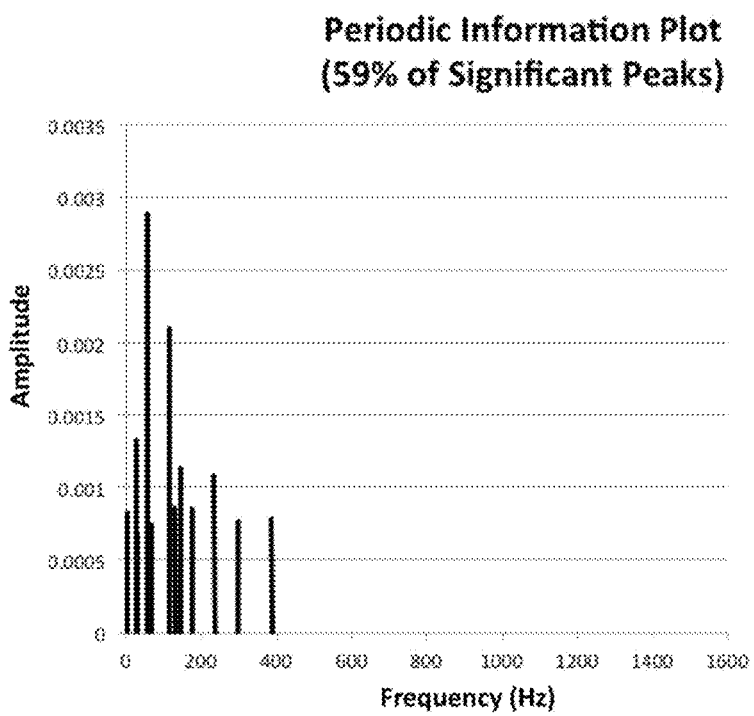

In one preferred embodiment of the second method, $Y_{THR}$ is set to only include a percentage of the largest peaks from the autocorrelation spectrum. The percentage may be calculated based on the percent periodic signal in the autocorrelation waveform. The percent periodic signal is calculated based on the autocorrelation coefficient, which is the square root of the Y-value of the largest peak in the autocorrelation waveform. For this method, only the percent periodic signal of the total number of autocorrelation spectrum peaks will be evaluated. An example of a PIP formed by this method, with $Y_{THR}$ set to 59%, is depicted in FIG. 12.

Figure 13:
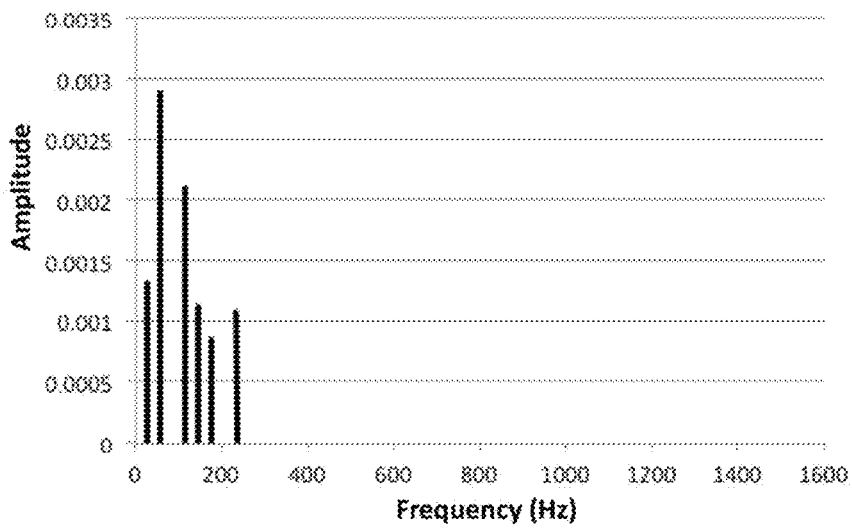

In another preferred embodiment of the second method, $Y_{THR}$ is set to include only peaks with values that are within the "percent periodic signal" of the largest peak value in the autocorrelation spectrum. These peaks, along with their harmonics that appear in the autocorrelation spectrum, will be utilized as the group of peaks to be intersected with those in the vibration spectrum to form the PIP. An example of a PIP formed by this method, with $Y_{THR}$ set to 59%, is depicted in FIG. 13.

Figure 14:
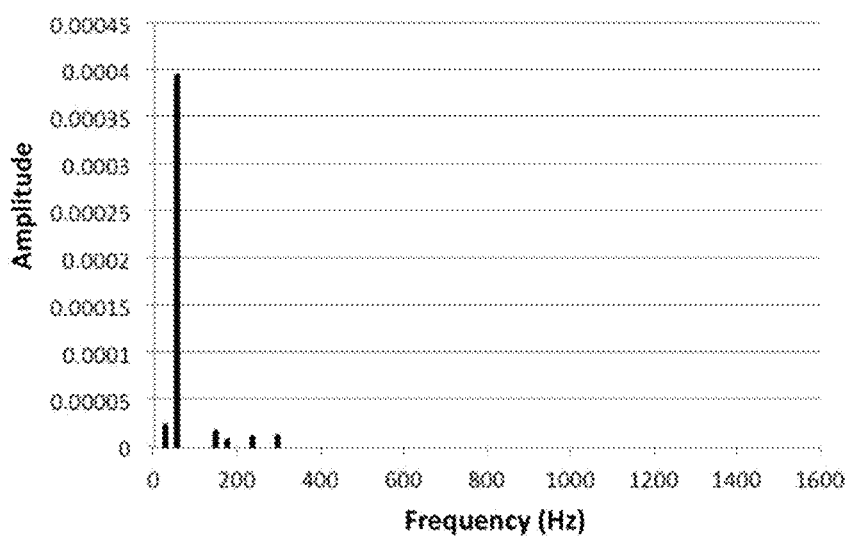

In a third method (step 76c), the PIP is determined according to the first method described above, and then the threshold of the second method is applied to the PIP according to:

$$\text{If } Y_{PIP1}(n) > Y_{THR}, Y_{PIP3}(n) = Y_{PIP1}(n) \qquad \text{Eq. (3a)}$$

$$\text{If } Y_{PIP1}(n) \leq Y_{THR}, Y_{PIP3}(n) = 0 \text{ (or some other default level)} \qquad \text{Eq. (3b)}$$

for n=1 to N. An example of a PIP formed by this method is depicted in FIG. 14.

Figure 15:
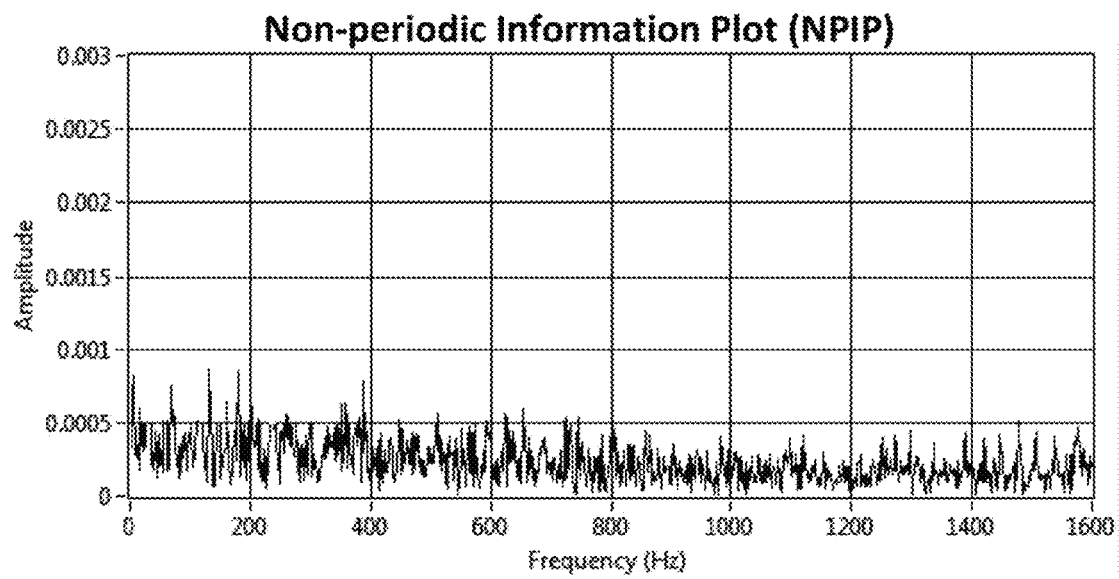

Some embodiments also derive a Non-periodic Information Plot (NPIP) that consists of only the Y-values of the autocorrelation spectrum that are less than a predetermined threshold (step 78). Thus, the NPIP includes only non-periodic components. An example of an NPIP formed by this method is depicted in FIG. 15.

Figure 16:
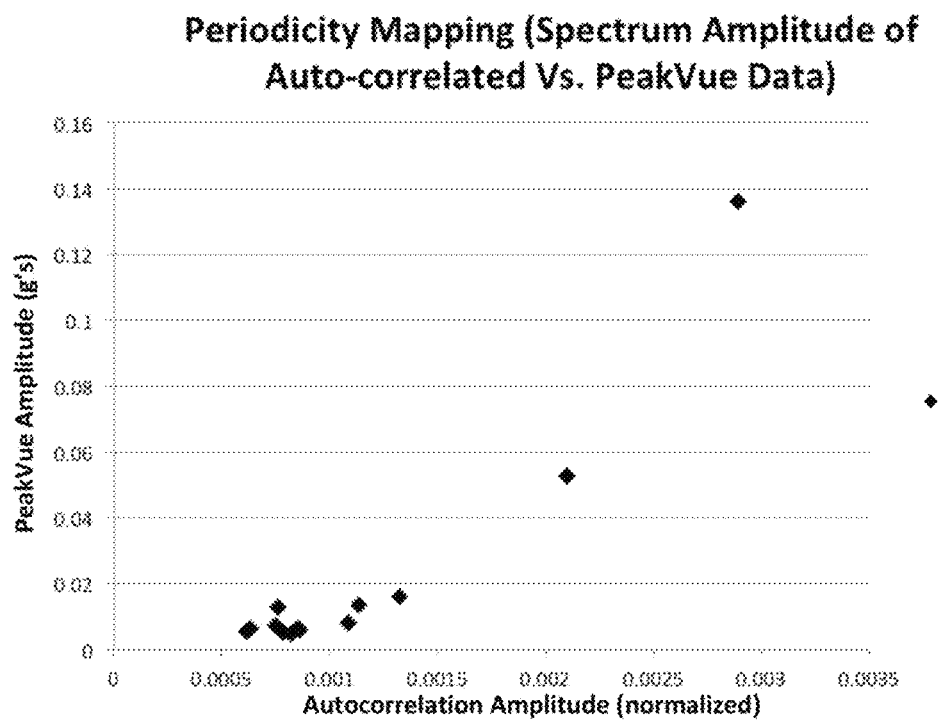

Some embodiments also derive a Periodicity Map from the vibration spectrum and the autocorrelation spectrum (step 82). The Periodicity Map is created by pairing the mathematically combined Y-values from the vibration spectrum and the autocorrelation spectrum corresponding to any given X-value of the autocorrelation spectrum. These pairs are plotted with the mathematically combined Y-value from the vibration spectrum $Y_{MCVS}(n)$ as the X-value of the point on the map $X_{PM}(n)$, and the Y-value from the autocorrelation spectrum $Y_{VS}(n)$ as the corresponding Y-value on the map $Y_{PM}(n)$, according to:

$$X_{PM}(n) = Y_{MCVS}(n) \qquad \text{Eq. (4a)}$$

$$Y_{PM}(n) = Y_{AS}(n) \qquad \text{Eq. (4b)}$$

for n=1 to N. As shown in FIG. 16, the resulting graph resembles a probability mapping. A specific software implementation would allow the user to run a cursor over each point to view the values creating that point.

Figure 17:
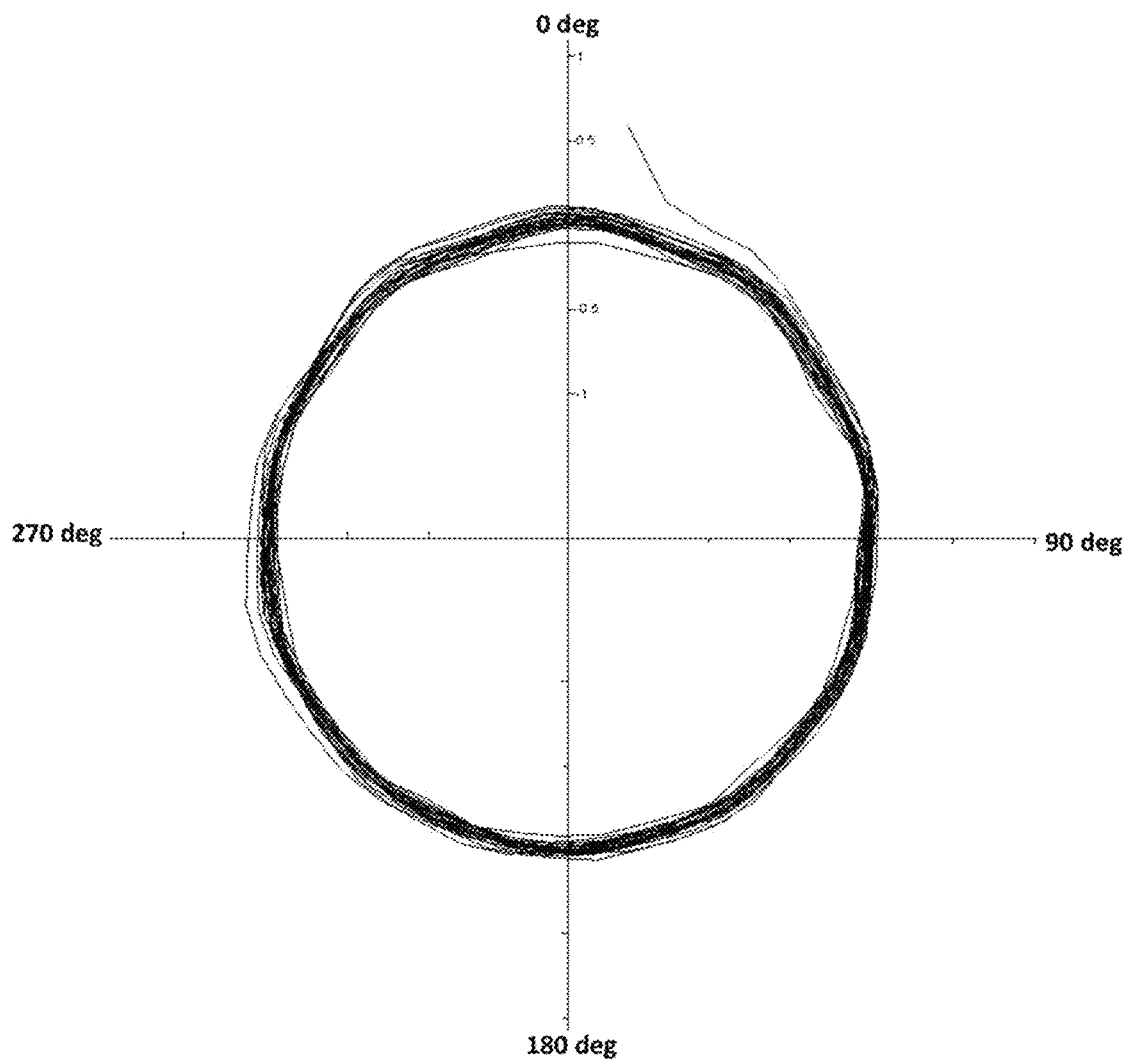

Some embodiments also derive a Circular Information Plot from any of the Periodic Information Plots described above (step 80). Once a linear PIP is calculated, an inverse FFT can be applied to generate an "information waveform." A Circular Information Plot can then be generated from this information waveform. An example of a Circular Information Plot formed by this method is depicted in FIG. 17.

Although preferred embodiments of the invention operate on vibration signals, the invention is not limited to only vibration signals. Periodic Signal Parameters and Periodic Information Plots may be derived from any signal containing periodic components.

PIP Generation—Second Embodiment

Figure 20:
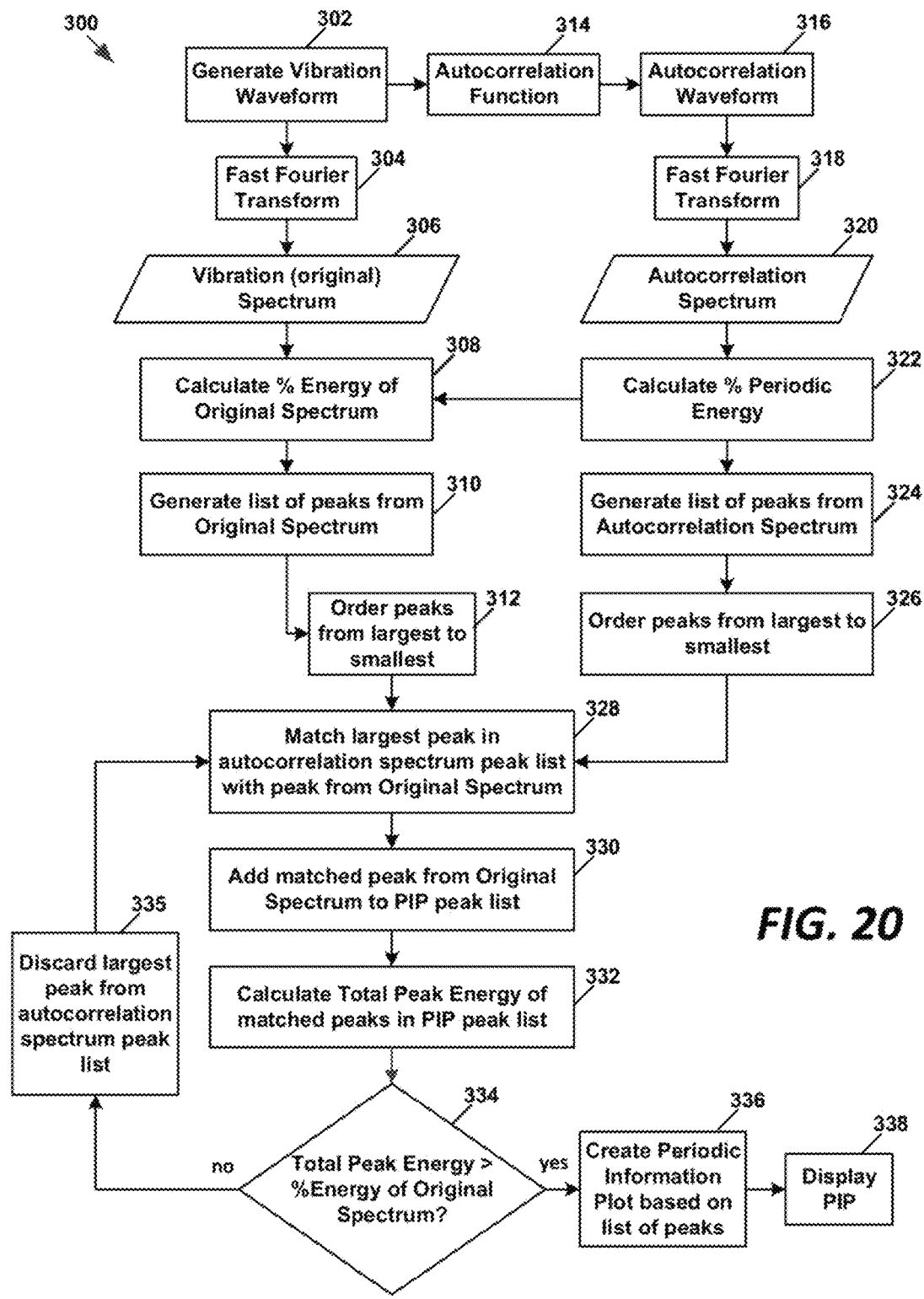
FIG. 20 depicts a flowchart of a method for generating a periodic information plot according to a second embodiment of the invention.

In a second embodiment, a signal is collected from plant equipment (i.e. rotating or reciprocating equipment) and is processed using the method 300 depicted in FIG. 20.

First, a waveform is generated (step 302 of FIG. 20), such as a vibration waveform acquired using the system depicted in FIG. 1A. If employing a high-pass filter and peak-hold decimation to an oversampled waveform to capture impacting information (such as using the PeakVue™ process), this may be a calculated waveform. An FFT of the vibration waveform is taken (step 304), resulting in a vibration spectrum 306 with frequency on the X-axis and amplitude on the Y-axis, an example of which is shown in FIG. 9. The vibration spectrum 306 is also referred to herein as the original spectrum to differentiate from the autocorrelation spectrum discussed hereinafter.

The waveform from step 302 is autocorrelated (step 314) to generate an autocorrelation waveform 316, having time on the X-axis and the correlation factor on the Y-axis. An FFT of the autocorrelation waveform 316 is calculated using the same Fmax as was used in the calculation of the FFF of the original waveform (step 318), resulting in an autocorrelation spectrum 320. Using the same Fmax forces the lines of resolution (LOR) of the autocorrelation spectrum 320 to be half of the LOR used in calculating the original spectrum 306. Since random events have largely been removed from the autocorrelation waveform 316, the remaining signal in the autocorrelation spectrum 320 is strongly related to periodic events. As shown in FIG. 10, the autocorrelation spectrum has frequency on the X-axis and amplitude related to the correlation factor on the Y-axis. Because the autocorrelation waveform's duration is half that of the original waveform, the associated autocorrelation spectrum has half the lines of resolution compared to the original spectrum.

Percent Periodic Energy (% Periodic Energy) is the percentage of energy in the original spectrum 306 that is related to periodic signals. It is calculated at step 322 based on the autocorrelation waveform 316 according to:

$$\% \text{ Periodic Energy} = \frac{}{\sqrt{\text{MaxPeak}(\text{after } 3\% \text{ of autocorrelation waveform})}}$$

In a preferred embodiment, the total energy of the original spectrum 306 is calculated as the square root of the sum of the squares of each bin value in the original spectrum 306 ranging from zero to Fmax. For purposes of finding bearing and/or gear teeth faults, the original spectrum 306 is the PeakVue spectrum.

The percent energy of the original spectrum 306 is calculated at step 308 according to:

% Energy of Original=Total energy of original spectrum×% Periodic Energy

A list of peaks from the original spectrum 306 is generated, wherein each listed peak is a located peak having a located frequency and an associated located amplitude (step 310). A list of peaks from the autocorrelation spectrum 320 is also generated, wherein each listed peak is a located peak having a located frequency and an associated located amplitude (step 324). In both lists, the peaks are arranged in order of descending amplitude, such that the peak having the largest amplitude is first in the list and the peak having the smallest amplitude is last (steps 312 and 326).

For the frequency value of each peak in the peak list generated for the autocorrelation spectrum, an associated matching peak is found in the peak list generated for the original spectrum (step 328). For a peak to "match," the frequency value of the peak from the original spectrum 306 must be within N×ΔFrequency of the frequency value of the peak from the autocorrelation spectrum 320, where in a preferred embodiment N=4 and ΔFrequency is expressed as:

$$\Delta \text{Frequency} = \frac{F\text{max of original spectrum}}{LOR \text{ of original spectrum}}.$$

Thus, a match exists when

|original peak frequency−autocorrelation peak frequency|≤N×ΔFrequency

For each matching peak from the original spectrum 306 found in step 328, the values of the located frequency and located amplitude is added to a PIP peak list (step 330). As each matching peak is added to the PIP peak list, a running Total Peak Energy value of all peaks in the PIP peak list is calculated (step 332). Because a Hanning window is used in the FFT calculation for this embodiment, the energy of a located peak is the result of energy from three bin values used in the creation of the located peak.

For each Total Peak Energy≤% Energy of Original, discard the associated peak in step 330 from the Autocorrelation Spectrum peak list before returning to step 328 (step 335).
This process of matching peaks and adding matched peaks to the PIP peak list continues until Total Peak Energy>% Energy of Original (step 334).

The Periodic Information Plot (PIP) is created by plotting the three points associated with each peak in the PIP peak list (step 336). In the preferred embodiment, the three points correspond to three bins associated with each located peak, assuming a Hanning window is used for FFT calculations. Examples of PIP's created using the method 300 of FIG. 20 are depicted in FIGS. 21 and 23-26.

Periodic Peaks

Periodic peaks in a spectrum are classified as either synchronous or non-synchronous peaks. Synchronous peaks are peaks that occur at the running speed of a shaft and its harmonic frequencies. For a gearbox having multiple shafts, there are also multiple families of synchronous peaks, wherein each family is associated with the speed of a particular shaft in the gearbox. In addition to running speed peaks, synchronous peaks associated with a gearbox also occur at all hunting tooth fundamental frequencies and their harmonics. Non-synchronous peaks are periodic families of harmonic peaks that are not members of a synchronous family. A family of non-synchronous, periodic peaks is most likely related to a bearing defect.

Because there may be many families of peaks related to either synchronous or non-synchronous peaks, a preferred embodiment provides a display color scheme to separate the different families of peaks. By color coding the different families in a spectrum, it is easy to distinguish between frequencies related to bearings (non-synchronous) and those related to running speed. In a gearbox, analysis of these running speed harmonic families (synchronous) can lead to the discovery of gear teeth problems. Using colors to designate the different families of peaks in a spectrum display or in the Periodic Information Plot simplifies the analysis for both the novice and experienced analyst.

Figure 21:
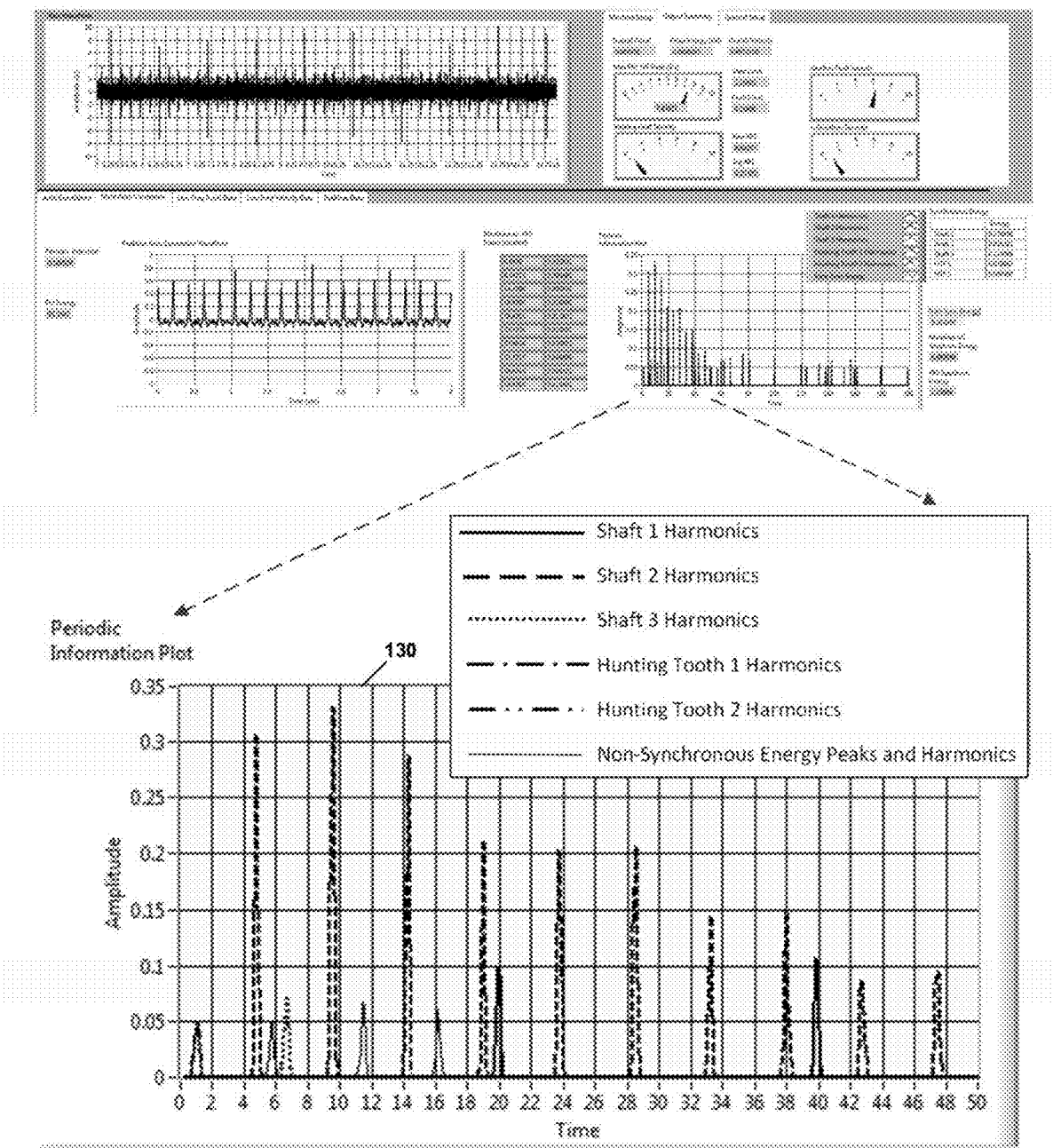
FIG. 21 depicts a graphical display of diagnostic information for a two-stage gearbox having a broken tooth on the bull gear of the second shaft.

FIG. 21 depicts an exemplary display indicating the presence of a broken tooth on a two-stage gearbox. The presence of synchronous and non-synchronous periodic peaks is notable in the Periodic Information Plot (PIP) 130. As indicated in the key provided in FIG. 21, synchronous families of peaks include the running speed fundamental and/or harmonics of "Shaft 1" highlighted in white (represented by large solid lines ——), "Shaft 2" highlighted in red (represented by long dash lines — —), and "Shaft 3" highlighted in green (represented by dotted lines ·········). Other synchronous families of peaks include hunting tooth fundamental frequencies and their harmonics "HTF 1" highlighted in blue (represented by dash-dot-dash-dot lines —·—·) and "HTF 2" highlighted in yellow (represented by dash-dot-dot lines —··—··). Non-synchronous families of peaks are highlighted in purple (represented by thin solid lines ——). It should be noted that the peaks shown in red (long dash lines) make up the overwhelming number of synchronous family of peaks, all related to the second shaft in the gearbox. In this example, the bull gear on the second shaft has a missing tooth.

Methods for Sorting and Discarding Statistically Outlying Peaks in the Autocorrelation Waveform (Step 34 in FIG. 2)

The following routine takes an array of data values, such as values of positive peaks in the autocorrelation waveform, and discards values outside the statistically calculated boundaries. In a preferred embodiment, there are four methods or criteria for setting the boundaries.

Method 1: Non-Conservative, Using Minimum and Maximum Statistical Boundaries

Consider an array of P values (or elements) where $P_0$ represents the number of values in the present array under evaluation. Now let $P_{-1}$ represent the number of values in the array evaluated a single step before $P_0$, let $P_{-2}$ represent the number of values in the array evaluated a single step before $P_{-1}$, and let $P_{-3}$ represent the number of values in the array evaluated a single step before $P_{-2}$.

Step 1

While evaluating the array of values for either the first time or $P_0 \neq P_{-1}$,

```
{
Calculate the mean (μ) and standard deviation (σ) for P₀
    If (nσ/μ) ≥ x, where x = 0, 1 and n = 1, 2 or 3 in the preferred embodiment, then
        include array values such that
        μ − nσ < values < μ + nσ
    Else
        STOP, values are within statistical boundaries.
    Endif
}
```

Step 2

If $P_0 \neq P_{-1}$, then
  While $P_{-1} \neq P_{-2}$, and $P_0 = P_{-1}$

```
{
Calculate the mean (μ) and standard deviation (σ) for P₀
    If (nσ/2μ) ≥ x, where x = 0, 1 and n = 1, 2 or 3 in the preferred embodiment, then
        include array values such that
        μ − nσ/2 < values < μ + nσ/2
    Else
        STOP, values are within statistical boundaries.
    Endif
}
Endif
```

Step 3

If $P_0 = P_{-1} = P_{-2}$, and $P_{-2} \neq P_{-3}$, then
  Calculate the mean (μ) and standard deviation (σ) for $P_0$
  Include array values such that

```
If P₀ = P₋₁ = P₋₂, and P₋₂ ≠ P₋₃, then
    Calculate the mean (μ) and standard deviation (σ) for P₀
    Include array values such that
    0.9μ < values < 1.1μ
Else
    STOP, values are within statistical boundaries.
Endif
```

Method 2: Non-Conservative, Using Maximum Statistical Boundary Only (No Minimum Boundary)

Use the same procedure as in Method 1 except only values exceeding the upper statistical boundaries are discarded. The minimum boundary is set to zero.

Method 3: Conservative, Using Minimum and Maximum Statistical Boundaries

Discard values based on Method 1, Step 1 only.

Method 4: Conservative, Using Maximum Statistical Boundary Only (No Minimum Boundary)

Discard values based on Method 1, Step 1 only and based on values exceeding the upper statistical boundaries. The minimum boundary is set to zero.

Example of Method 1 for Sorting Out Statistical Outliers

As an example of the sorting Method 1, consider an original set of values, $P_0$, containing the twenty-one values listed below in Table 3 below, with n=1.

TABLE 3

| |
|---|
| 0.953709 |
| 0.828080 |
| 0.716699 |
| 0.653514 |
| 0.612785 |
| 0.582031 |
| 0.579209 |
| 0.557367 |
| 0.545801 |
| 0.495215 |
| 0.486426 |
| 0.486053 |
| 0.475123 |
| 0.472348 |
| 0.467129 |
| 0.465488 |
| 0.446327 |
| 0.440497 |
| 0.437959 |
| 0.427256 |
| 0.411627 |

The mean (μ) of this original set, $P_0$, is 0.54955 and standard deviation (σ) is 0.13982. Therefore, in Step 1 of Method 1, $$\frac{n\sigma}{\mu} = 1 * \frac{0.13982}{0.54955} = 0.25442.$$

Since 0.25442 is greater than 0.1, calculate $$\mu - n\sigma = 0.54955 - 1 * 0.13982 = 0.409735$$

and $$\mu + n\sigma = 0.54955 + 1 * 0.13982 = 0.689373.$$

Next, define the set $P_{-1} = P_0$ and define a new set $P_0$, the values of which are all the values of $P_{-1}$ that are between the values $\mu + \sigma = 0.689343$ and $\mu - \sigma = 0.409735$. The set $P_0$ now contains the values listed below in Table 4, wherein three outlier values have been eliminated.

TABLE 4

| |
|---|
| 0.653514 |
| 0.612785 |
| 0.582031 |
| 0.579209 |
| 0.557367 |
| 0.545801 |
| 0.495215 |
| 0.486426 |
| 0.486053 |
| 0.475123 |
| 0.472348 |
| 0.467129 |
| 0.465488 |
| 0.446327 |
| 0.440497 |
| 0.437959 |
| 0.427256 |
| 0.411627 |

Since $P_0 \neq P_{-1}$, Step 1 is repeated, where for the set $P_0$:

$\mu = 0.50234,$ $\sigma = 0.06946,$ $\sigma/\mu = 0.138263,$ $\mu + \sigma = 0.571797,$ and $\mu - \sigma = 0.432887.$ Now define the set $P_{-2} = P_{-1}$, and $P_{-1} = P_0$ and define a new set $P_0$, the values of which are all the values of $P_{-1}$ that are between the values $\mu + \sigma = 0.571797$ and $\mu - \sigma = 0.432887$. The set $P_0$ now contains the values listed below in Table 5, wherein four more outlier values have been eliminated.

TABLE 5

| |
|---|
| 0.557367 |
| 0.545801 |
| 0.495215 |
| 0.486426 |
| 0.486053 |
| 0.475123 |
| 0.472348 |
| 0.467129 |
| 0.465488 |
| 0.446327 |
| 0.440497 |
| 0.437959 |

Since $P_0 \neq P_{-1}$, Step 1 is repeated, where for the set $P_0$:

$\mu = 0.481311,$ $\sigma = 0.037568,$ and $\sigma/\mu = 0.078053.$

Since $\sigma/\mu = 0.078053 \leq 1,$ all the members of the array $P_0$ are statistically close in value and need no more sorting.

If at any point in the calculations $P_0 = P_{-1}$ and $P_{-1} \neq P_{-2}$, then Step 2 would be executed instead of Step 1. In the example above, since $P_0 \neq P_{-1}$ for every iteration, only Step 1 was necessary for the calculations.

Predicting Bearing Faults Based on Periodic Signal Parameter (PSP)

Figure 22:
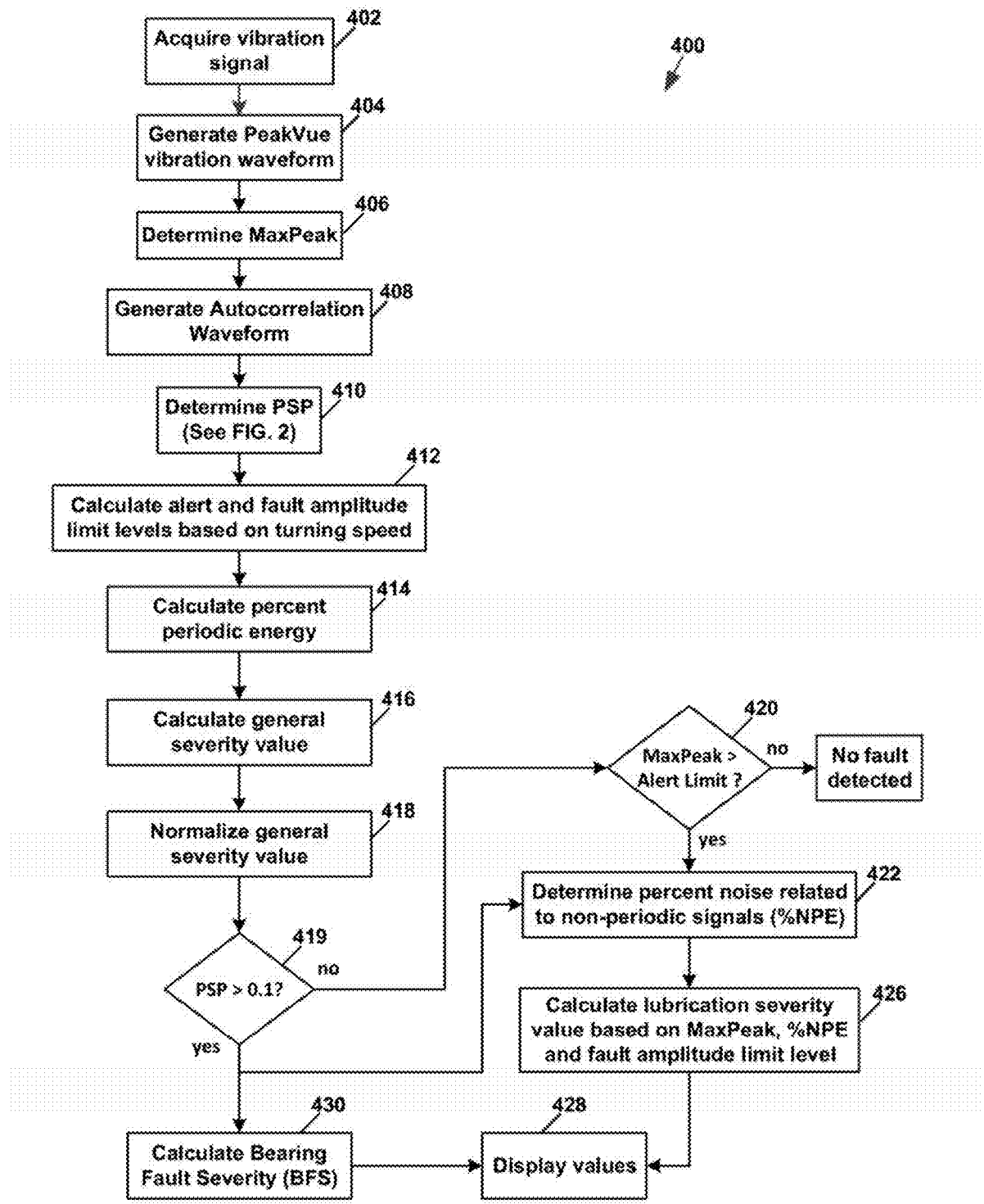
FIG. 22 depicts a flowchart of a method for determining a bearing fault severity value and a lubrication severity value according to a preferred embodiment of the invention.

FIG. 22 depicts steps in a preferred embodiment of a method 400 for generating bearing fault condition information. A time-domain oversampled vibration waveform is measured (step 402), such as using the accelerometer 104 or other sensor attached to the machine 102 being monitored. A PeakVue™ waveform is then generated (step 404), such as by high-pass filtering and peak-hold decimating the oversampled waveform. The maximum peak amplitude (MaxPeak) of the PeakVue™ waveform is determined (step 406), and its associated autocorrelation waveform is calculated (step 408). Based on the autocorrelation waveform, the periodic signal parameter (PSP) is calculated according to the method depicted in FIG. 2 (step 410).

Figure 28:
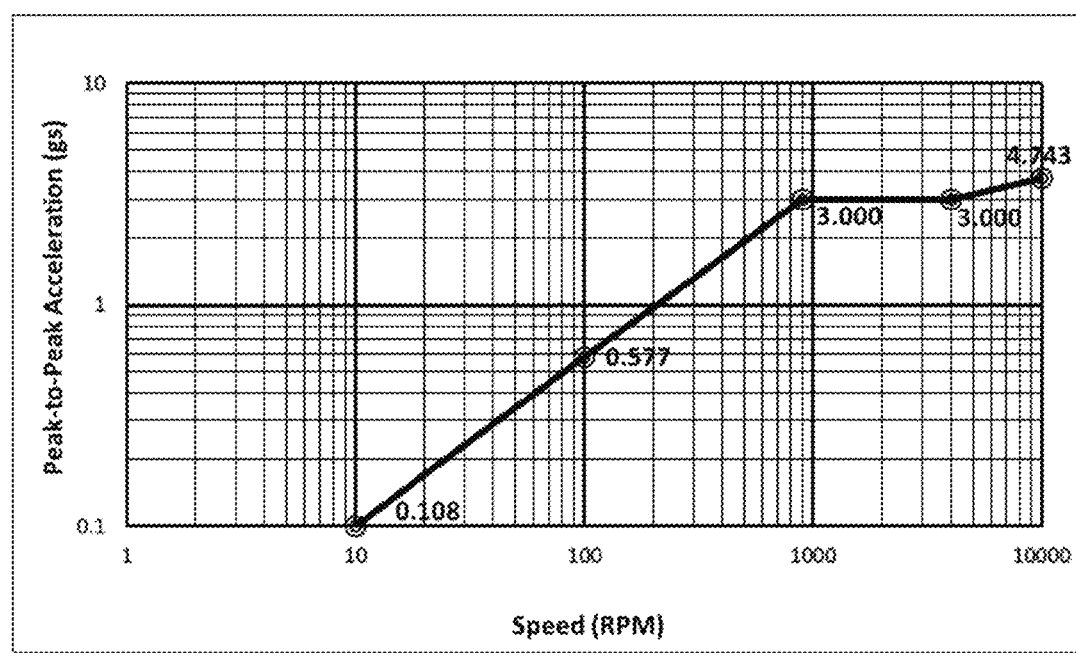
FIG. 28 depicts an exemplary graph of representative alert levels for a PeakVue waveform for an inner race bearing fault determined according to one embodiment.

In a preferred embodiment, alert amplitude limit levels (in g's) are determined based on the nominal turning speed according to the relationship depicted in FIG. 28 (step 412). Fault amplitude limit levels are preferably two times the alert levels. FIG. 28 provides a graphical representation of one method for determining alert limits for a PeakVue signal based on the RPM of the machine shaft. The alert level would be compared to the peak value occurring in the PeakVue waveform and applies for a developing inner race fault. It will be appreciated that the alert limit levels depicted in FIG. 28 are suggestions only, and the analyst may decide to use values that have been determined to be optimal for their machine. In some situations, the analyst may start out using the values from FIG. 28, and then adjust them based on experience.

Figure 19:
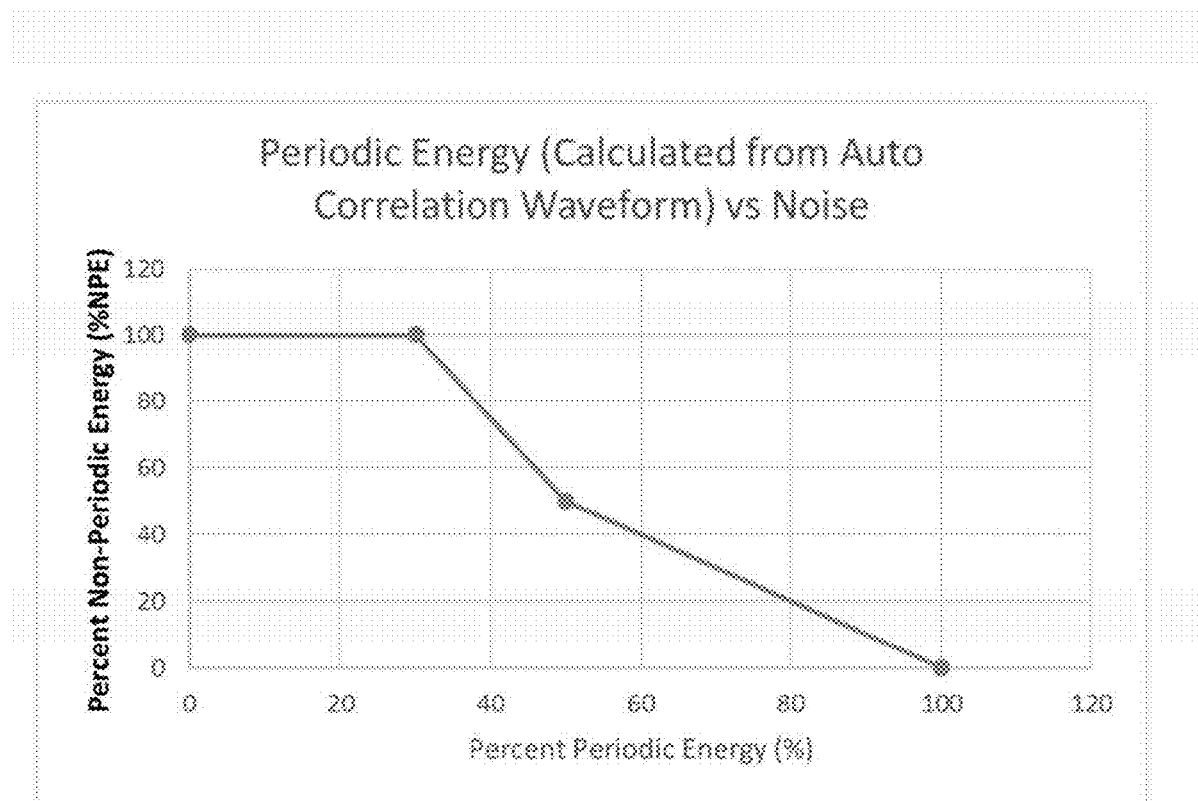
FIG. 19 depicts a plot of energy calculated from an autocorrelation waveform in relation to random vibration noise and other non-periodic energy present in a vibration signal.

Before calculations of severity values can be made, Percent Periodic Energy must be calculated. Percent Periodic Energy (step 414) is calculated from the autocorrelation waveform according to:

$$\% \text{ Periodic Energy} = \sqrt{\text{MaxPeak(afterfirst3\%)}}$$

wherein the maximum peak in the autocorrelation waveform does not include the first 3% of the waveform. Generally, the Percent Periodic Energy calculation is not as accurate for values less than 50%. Accordingly, as indicated in FIG. 19, the slope of the function for values less than 50% is greater than 1.0. Therefore, the percent periodicity is not determined for values less than 50%. A general severity value is necessary for all severity estimates, which is calculated according to:

$$\text{General Severity} = \frac{\text{MaxPeak}}{2 \times \text{Fault Limit}} \text{(step 416)}.$$

In a preferred embodiment, the severity value is normalized by multiplying the result of step 416 by a desired maximum gauge value x according to:

Normalized General Severity = General Severity × x (step 418).

Figure 18:
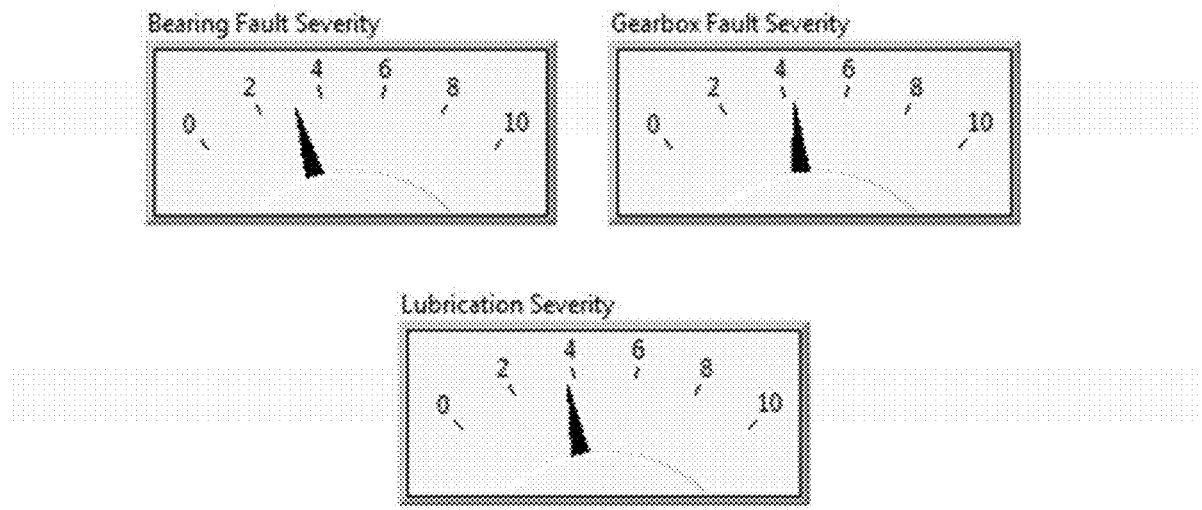
FIG. 18 depicts a graphical representation of diagnostic fault condition gauges according to a preferred embodiment.

For the gauges shown in FIG. 18, where x=10,

Normalized General Severity = General Severity × 10.

If the PSP is greater than 0.1 (step 419), a bearing fault is possibly present. Bearing Fault Severity (BFS) may be calculated according to:

BFS=Normalized Severity×% Periodic Energy (step 430).

If the resulting answer is greater than x (10 in this example), then the answer is truncated to be x.

In some embodiments, knowledge of the turning speed improves confidence that the periodicity is related to bearing faults and not turning speed incidences. When the turning speed is known, periodic peaks from the periodic information plot (PIP) can be classified as synchronous and non-synchronous. If only synchronous peaks are present, no bearing fault is indicated. If significant non-synchronous peaks are present, a possible bearing issue is confirmed, as indicated by:

$$BFS = \text{Normalized Severity} \times \left[\left(\frac{(\text{energy of the located nonsynchronous peaks})^2}{(\text{total energy of the associated } PeakVue \text{ spectrum})^2}\right)\right].$$

If PSP≤0.1 and MaxPeak is <alert level, no fault is indicated by the measurement, meaning the asset is in good condition.

If PSP is less than or equal to 0.1 and MaxPeak is greater than the alert amplitude limit level (step 420), a deficiency in bearing lubrication is indicated. In addition, there may be lubrication issues when a bearing fault is present. (This is shown in FIG. 22 with an arrow going from between steps 419 and 430 to step 422.) The severity of the lubrication problem is generally dependent upon the MaxPeak value of the originating waveform (step 406) and the Percent Non-Periodic Energy (% NPE) indicated from the associated autocorrelation waveform (step 408).

As shown in FIG. 19, Percent Non-periodic Energy (% NPE) is a function of Percent Periodic Energy and can be determined using the plot of FIG. 19 (step 422). Percent Periodic Energy (% Periodic Energy) is defined as the percentage of energy in the PeakVue (original) spectrum that is related to periodic signals. % NPE is defined as the percentage of energy in the PeakVue (original) spectrum that is related to random vibration signals.

The Lubrication Severity (LS) value is determined according to:

$$LS = \frac{\text{MaxPeak}}{2 \times \text{Fault Limit}} \times x \times \% \ NPE,$$

where x is the normalization value (step 426). For the Lubrication Severity gauge shown in FIG. 18, x=10. If the resulting value is greater than x (10 in this example), then the value is truncated to be x.

In an alternative embodiment, instead of determining whether PSP is greater than 0.1 in step 114, it is determined whether % Periodic Energy is greater than Y, where in most cases Y is 50%.

While the preferred embodiment of the algorithm described above and depicted in FIG. 22 uses a PeakVue waveform, the algorithm could be applied to any waveform generated from any type of signal, such as vibration, current, ultrasonic, etc.

Figure 23:
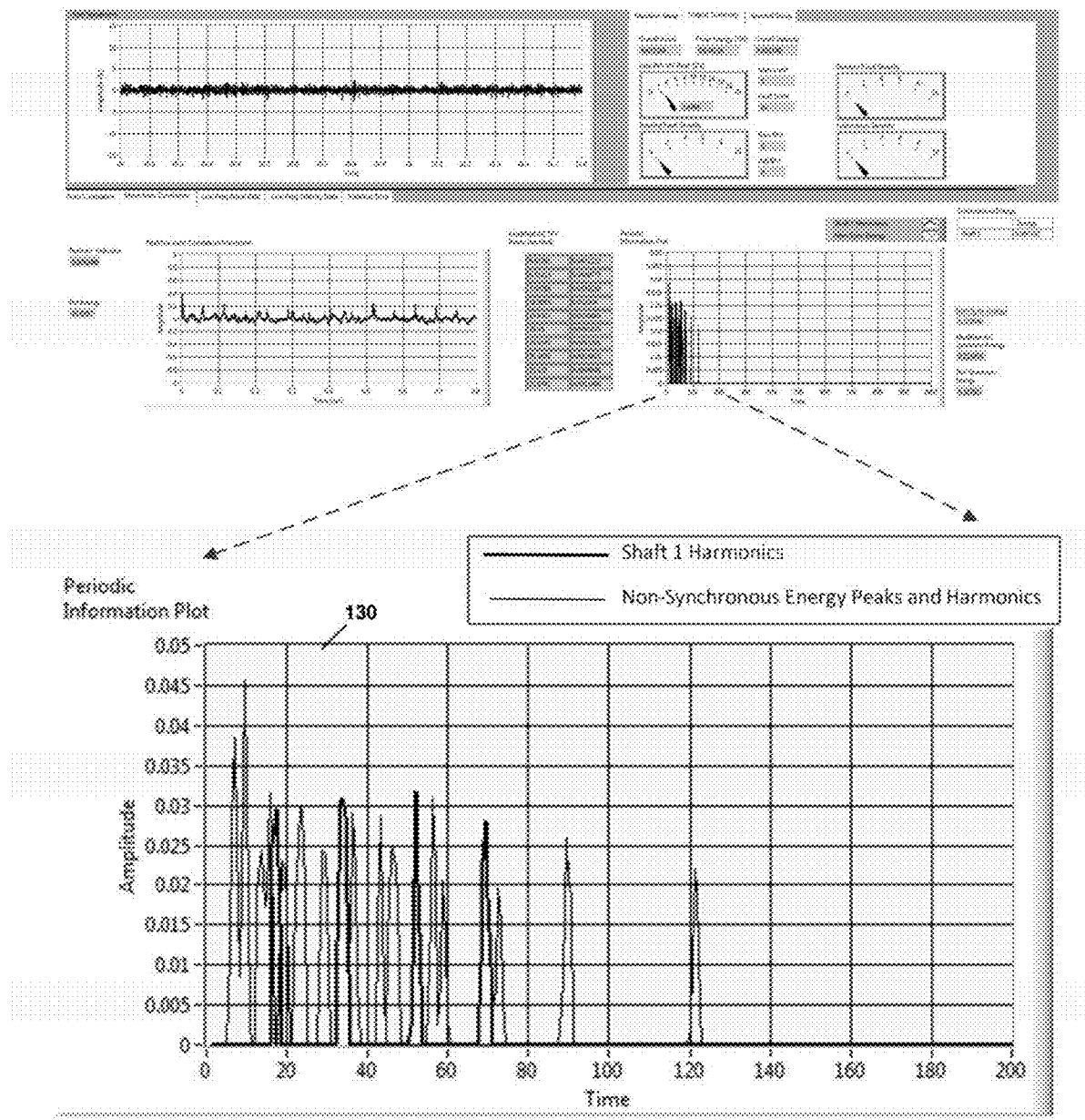
FIG. 23 depicts a graphical display of diagnostic information for a fully-lubricated bearing having no faults.

Following are four examples that demonstrate use of the algorithm of FIG. 22 to determine the status of a bearing under different conditions. FIG. 23 depicts the results for a new, fully-lubricated bearing with no faults. As shown, the gauges for Bearing Fault Severity and Lubrication Severity both indicate a value of zero because the bearing is new and in good condition.

Figure 24:
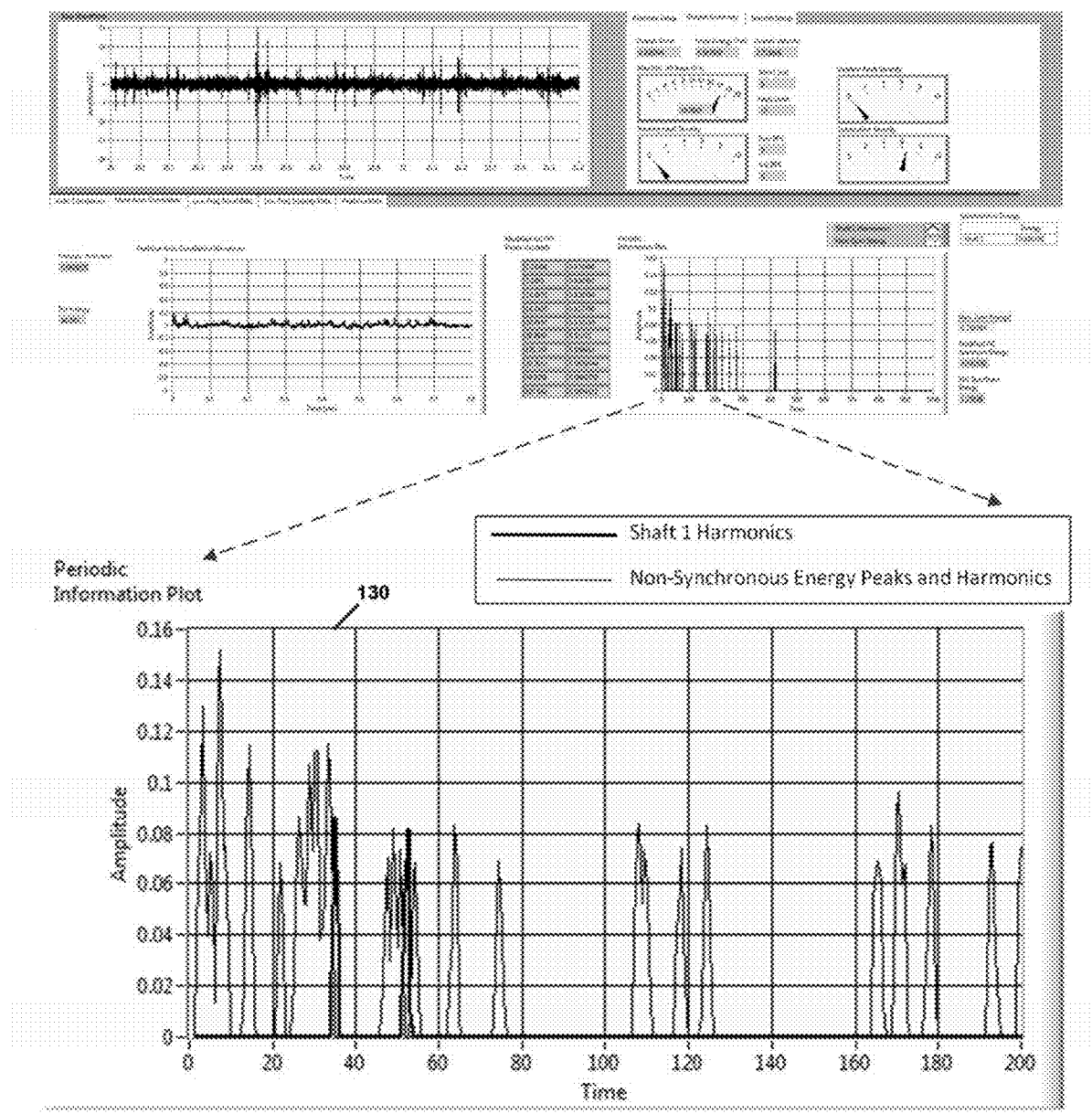
FIG. 24 depicts a graphical display of diagnostic information for a good bearing with no significant faults other than it is running "dry" due to a lack of lubrication.

FIG. 24 depicts the results for a bearing with no faults other than it is running "dry" because there is insufficient lubrication present in the bearing. As shown, the Bearing Fault Severity is still zero but the Lubrication Severity is about 6.5. In this example, the % Periodic Energy is 44.3%. The resulting % NPE based on FIG. 19 is 77.85%. It should be noted that the PSP is 0.0618.

Figure 25:
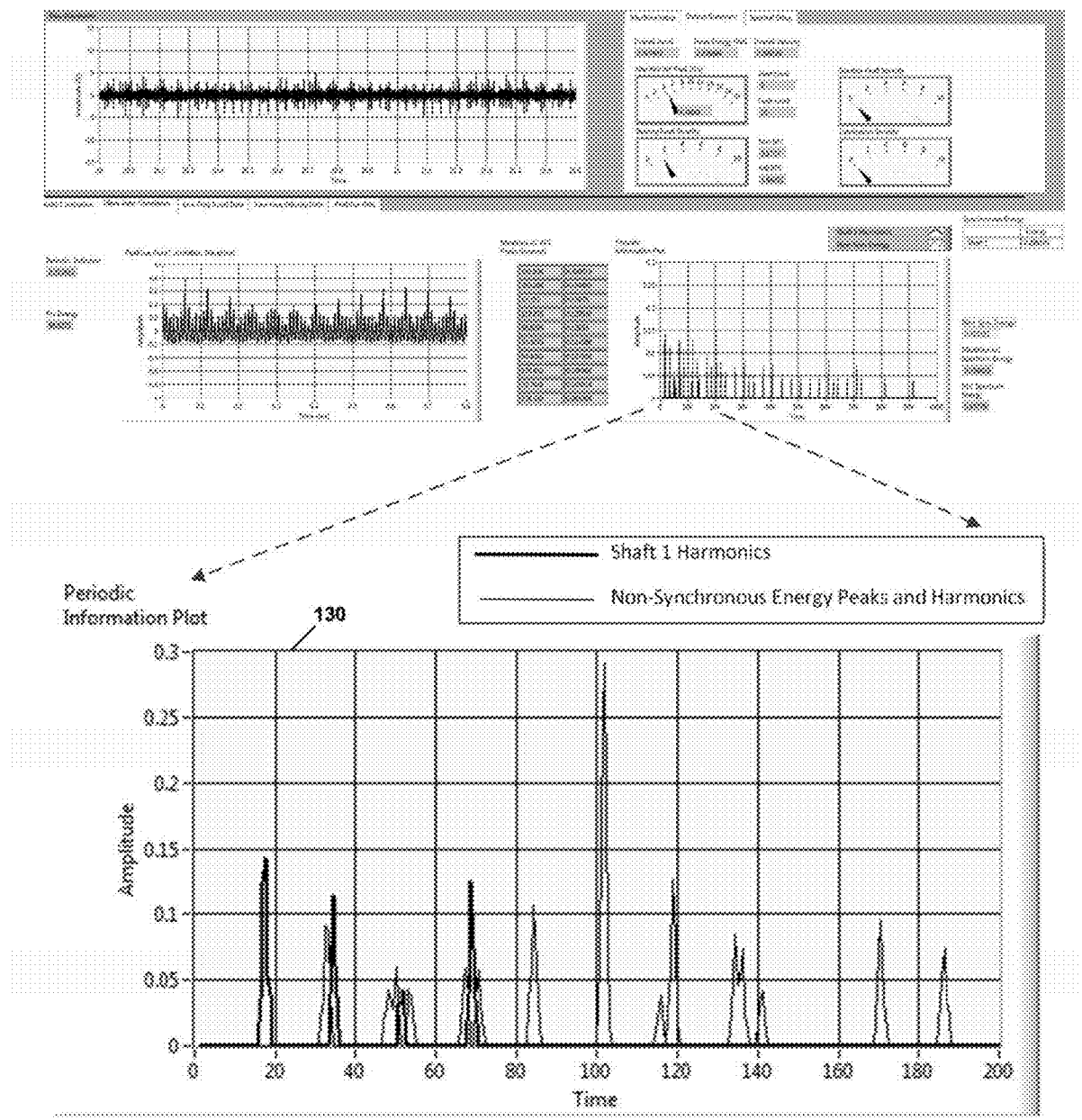
FIG. 25 depicts a graphical display of diagnostic information for a fully-lubricated bearing having an inner race fault.

FIG. 25 depicts the results for a bearing with a small inner race fault and no lubrication problems. As shown, the Bearing Fault Severity is slightly elevated to about 1.4, but the Lubrication Severity is close to zero. In this example, the % Periodic Energy is 88.8%. Based on FIG. 19, the resulting % NPE is 11.2%. It should be noted that the PSP is 0.213 for this example.

Figure 26:
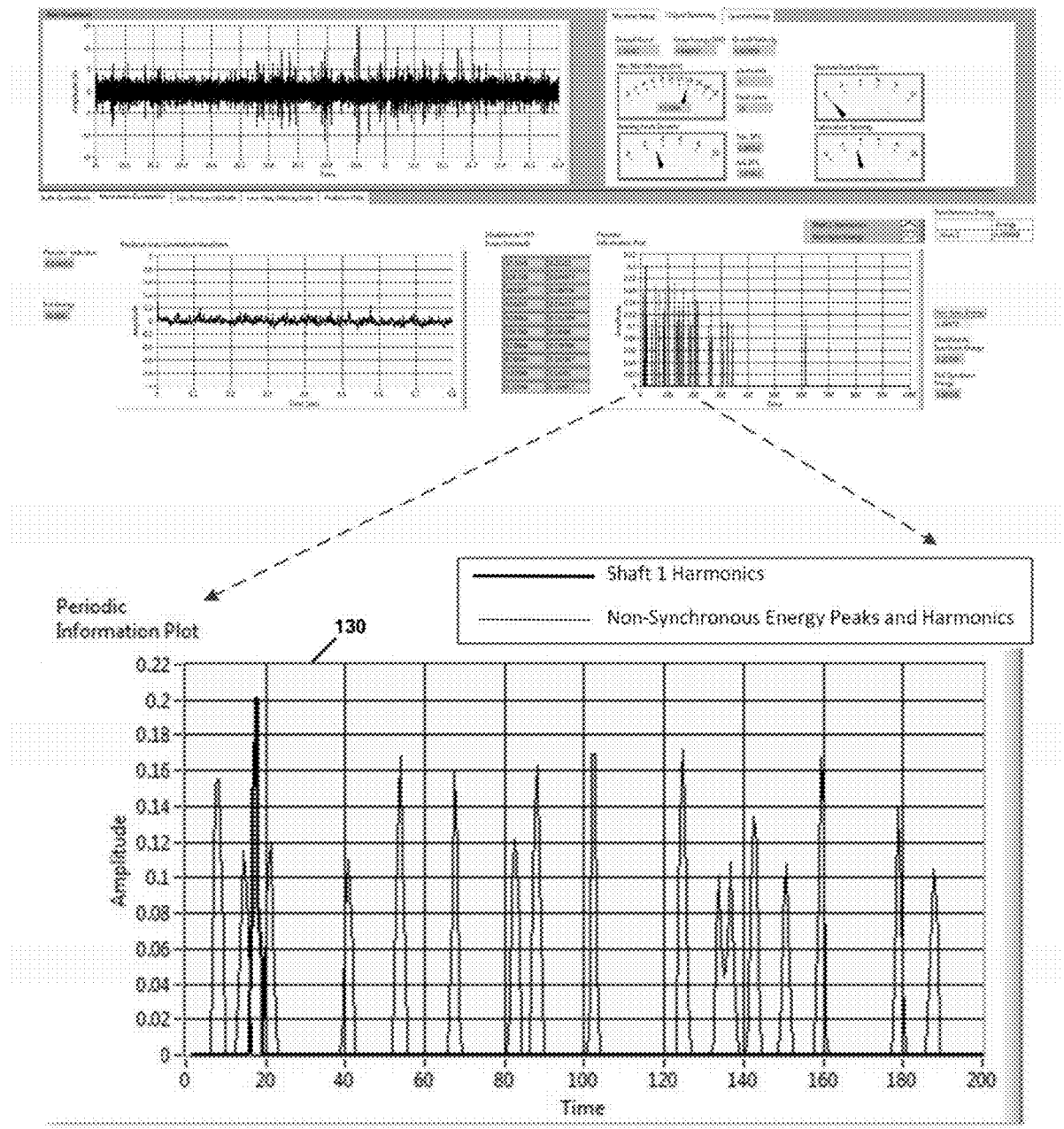
FIG. 26 depicts a graphical display of diagnostic information for a bearing having an inner race fault, and which is running "dry" due to a lack of lubrication.

FIG. 26 depicts the results for a bearing with a small inner race fault as well as a lubrication problem due to the fact that the bearing is running "dry." Even though PSP is 0.074, % Periodic Energy is 51%. Therefore, the signal has some periodicity. As shown, the Bearing Fault Severity is almost 3, while the Lubrication Severity is around 3.25. Those skilled in the art will appreciate that this diagnostic result is an advancement in technology, and could not be determined by other available algorithms. The ability to isolate the lower amplitude non-synchronous signals caused by the mechanical damage to the bearing from the non-periodic energy generated by lack of lubrication, which is significantly higher in amplitude, has not previously been available.

Predicting Gearbox Faults Based on Periodic Signal Parameter (PSP)

FIG. 21 depicts steps in a preferred embodiment of a method 200 for generating gearbox fault condition information. A time-domain oversampled vibration waveform is measured, such as using the accelerometer 104 or other sensor attached to the machine 102 being monitored (step 202). A PeakVue™ waveform is then generated, such as by high-pass filtering and peak-hold decimating the over-sampled waveform (step 204). The maximum peak amplitude (MaxPeak) of the PeakVue™ waveform is determined (step 206), and its associated autocorrelation waveform is calculated (step 208). Based on the autocorrelation waveform, the periodic signal parameter (PSP) is calculated according to the method depicted in FIG. 2 (step 210).

The rotational speed of at least one of the shafts in the gearbox is measured, such as using a tachometer (step 212), and the speed of each of the other shafts in the gearbox is calculated based on the speed measured in step 212 and knowledge of the gear ratios for the other shafts (step 214). In addition, based on shaft running speeds, hunting tooth frequencies are calculated based on techniques known to those of ordinary skill in the art. In a preferred embodiment, alert amplitude limit levels (in g's) are determined based on the nominal turning speed according to the relationship depicted in FIG. 28, or based on the analyst's experience, or both, as discussed above (step 216). Fault amplitude limit levels are preferably two times the alert levels.

Before calculations of specific severity values can be made, Percent Periodic Energy must be calculated. In a preferred embodiment, Percent Periodic Energy is calculated from the autocorrelation waveform according to:

% Periodic Energy=√{MaxPeak(afterfirst3%)} wherein the MaxPeak of the autocorrelation waveform does not include the first 3% of the waveform (step 218). Generally, the Percent Periodic Energy calculation is not as accurate for values less than 50%. Accordingly, as indicated in FIG. 19, the slope of the function for values less than 50% is greater than 1.0.

In order to calculate severity values for different faults, a general severity value is determined. General Severity may be calculated according to:

$$\text{General Severity} = \frac{\text{MaxPeak}}{2 \times \text{Fault Limit}} \text{(step 220)}.$$

The severity value is normalized by multiplying the result of step 220 by a desired maximum gauge value x according to:

Normalized General Severity=General Severity×x (step 222).

For the gauge shown in FIG. 18, where x=10,

Normalized General Severity=General Severity×10.

The PIP is generated using the procedure described herein with reference to FIG. 20 (step 224).

If the PSP is greater than 0.1 (step 225), periodic frequencies related to the gearbox and/or bearings are present.

Based on knowledge of the turning speed, periodic peaks from the periodic information plot (PIP) can be classified as synchronous and non-synchronous. If non-synchronous peaks are present in the PIP (step 226), a bearing fault severity (BFS) value may be calculated (step 228) and displayed (step 234) according to:

$$BFS = \text{Normalized severity}$$
$$\text{(step 222)} \times \left[ \left( \frac{(\text{energy of the located nonsynchronous peaks})^2}{(\text{total energy of the associated } PeakVue \text{ spectrum})^2} \right) \right].$$

If synchronous peaks are present (step 230) and fault limits are exceeded, gear teeth degradation is indicated. A gearbox fault severity (GFS) value may be calculated (step 232) and displayed (step 234) according to:

$$GFS = \text{Normalized severity}$$
$$\text{(step 222)} \times \left[ \left( \frac{(\text{energy of the located synchronous peaks})^2}{(\text{total energy of the associated } PeakVue \text{ spectrum})^2} \right) \right].$$

If the resulting answer is greater than x (10 in this example), then the answer is truncated to be x.

If PSP≤0.1 and Max Peak is <alert level, no fault is indicated by the measurement, meaning the asset is in good condition.

Figure 27:
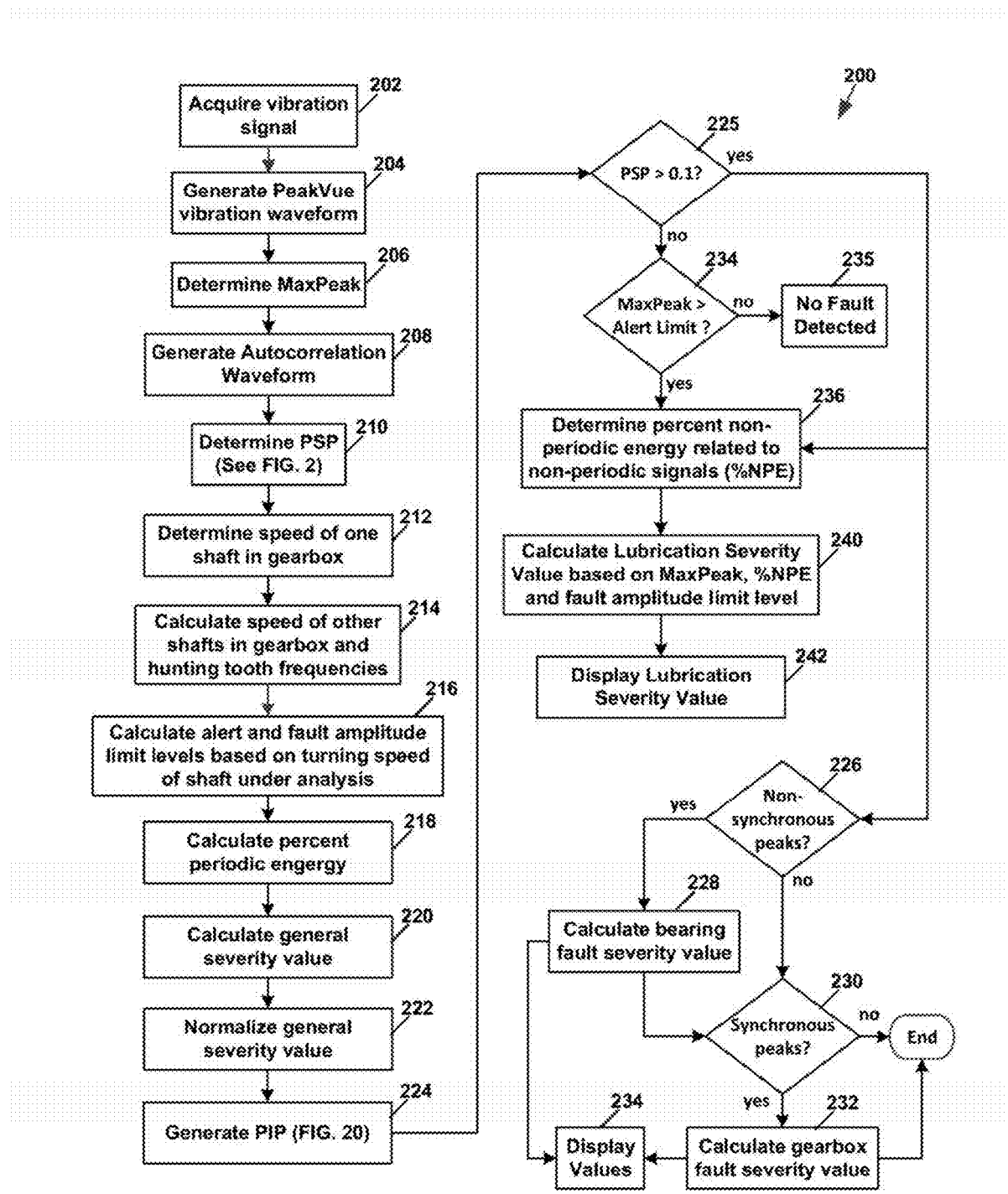
FIG. 27 depicts a flowchart of a method for determining a bearing fault severity value, a gearbox fault severity value, and a lubrication severity value according to a preferred embodiment of the invention.

If PSP is less than or equal to 0.1 and MaxPeak is greater than the alert amplitude limit level (step 234), a deficiency in bearing and/or gearbox lubrication is indicated. In addition, there may be lubrication issues along with mechanical faults present. (This is shown in FIG. 27 by an arrow going from between steps 225 and 226 to step 236). The severity of the lubrication problem is generally dependent upon the MaxPeak value of the originating waveform (step 206) and the Percent Non-periodic energy (% NPE) indicated from the associated autocorrelation waveform (step 208).

As discussed above, Percent Non-periodic energy (% NPE) is a function of Percent Periodic Energy and can be determined using the plot of FIG. 19 (step 236). Percent Periodic Energy (% Periodic Energy) is defined as the percentage of energy in the PeakVue (original) spectrum that is related to periodic signals. Percent Non-periodic energy is defined as the percentage of energy in the PeakVue (original) spectrum that is related to random vibration signals.

The bearing or gearbox lubrication severity value is determined and displayed according to:

$$\text{Lubrication Severity} = \frac{\text{MaxPeak}}{2 \times \text{Fault Limit}} \times x \times \% \ NPE,$$

where x is the normalization value (steps 240 and 242). For the Lubrication Severity gauge shown in FIG. 18, x=10. If the resulting value is greater than x (10 in this example), then the value is truncated to be x.

In an alternative embodiment, instead of determining whether PSP is greater than 0.1 in step 218, it is determined whether % Periodic Energy is greater than Y, where in most cases Y is 50%.

The foregoing description of preferred embodiments for this invention has been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for acquiring and analyzing periodic information in vibration associated with a machine, the apparatus comprising:
    a vibration sensor securely attached to the machine in a location providing a solid transmission path from a source of vibration within the machine to the vibration sensor, the vibration sensor for generating a vibration signal;
    a data collector in communication with the vibration sensor, the data collector configured to receive and condition the vibration signal, the data collector comprising:
        an analog-to-digital converter for converting the vibration signal to digital vibration data; and
        memory for buffering the digital vibration data; and
    a periodic information processor operable to receive the digital vibration data, the periodic information processor configured to execute operational instructions for processing the digital vibration data, the operational instructions comprising instructions which, when executed:
        generate a vibration waveform based on the digital vibration data;
        perform an autocorrelation function on the vibration waveform to generate an autocorrelation waveform;
        perform a Fast Fourier Transform on the vibration waveform to generate a vibration spectrum;

perform a Fast Fourier Transform on the autocorrelation waveform to generate an autocorrelation spectrum;
compile a first list of amplitude peaks from the vibration spectrum;
compile a second list of amplitude peaks from the autocorrelation spectrum;
match autocorrelation amplitude peaks in the second list with vibration amplitude peaks in the first list;
generate a peak list that includes each vibration amplitude peak to the peak list that matches an autocorrelation amplitude peak;
as vibration amplitude peaks are added to the peak list, determine a total amount of peak energy associated with the vibration amplitude peaks in the peak list; and
after the total amount of peak energy associated with the vibration amplitude peaks in the peak list exceeds a predetermined threshold, generate a periodic information plot comprising the vibration amplitude peaks in the peak list.

2. The apparatus of claim 1 wherein the periodic information processor generates the periodic information plot having at least 80% fewer data points than the vibration spectrum.

3. The apparatus of claim 1 wherein the predetermined threshold comprises a percent energy value, and wherein the periodic information processor is configured to execute operational instructions for calculating the percent energy value according to % Energy of Original=Total energy of vibration spectrum×% Periodic Energy wherein $$\% \text{ Periodic Energy} = \frac{}{\sqrt{MaxPeak \text{ (after first 3\% of autocorrelation waveform)}}}$$

and wherein MaxPeak (after 3% of waveform) comprises a maximum absolute peak in the autocorrelation waveform occurring outside the first 3% of the autocorrelation waveform.

4. The apparatus of claim 1 wherein the vibration waveform is a PeakVue waveform.

5. The apparatus of claim 1 wherein the periodic information processor is configured to execute operational instructions to arrange the amplitude peaks in the first and second lists in order of descending amplitude, such that a largest amplitude peak is first and a smallest amplitude peak is last.

6. The apparatus of claim 1 wherein the periodic information processor is configured to execute operational instructions to classify the amplitude peaks as synchronous peaks and nonsynchronous peaks, to assign one or more first display colors to the synchronous peaks in the periodic information plot, and to assign one or more second display colors to the nonsynchronous peaks in the periodic information plot, wherein the first display colors are different from the second display colors.

7. The apparatus of claim 1 wherein the periodic information processor is configured to execute operational instructions to separate amplitude peaks that are synchronous peaks into multiple families and to assign a different display color to each family of synchronous peaks in the periodic information plot.

8. The apparatus of claim 1 further comprising:
a data communication network to which the periodic information processor is connected and through which the periodic information plot is communicated; and
an analyst computer connected to the data communication network, the analyst computer for receiving and displaying the periodic information plot for viewing by an analyst.

9. The apparatus of claim 1 wherein the periodic information processor determines a match between an autocorrelation amplitude peak from the second list and a vibration amplitude peak from the first list when

|vibration peak frequency−autocorrelation peak frequency|≤$n$×ΔFrequency, where the vibration peak frequency is a frequency value of the vibration amplitude peak from the first list, the autocorrelation peak frequency is a frequency value of the autocorrelation amplitude peak from the second list, n is an integer value, and ΔFrequency is determined according to:

$$\Delta \text{Frequency} = \frac{F\text{max of vibration spectrum}}{LOR \text{ of vibration spectrum}},$$

where Fmax is the maximum frequency of the vibration spectrum and LOR is the number of lines of resolution in the vibration spectrum.

10. The apparatus of claim 1 wherein the data collector comprises a digital data recorder or a vibration data collector.

11. The apparatus of claim 1 wherein the data collector includes a low-pass anti-aliasing filter.

12. The apparatus of claim 1 wherein the periodic information processor is a component of the data collector.

13. The apparatus of claim 1 wherein the periodic information processor is a component of an analyst computer that is in communication with the data collector via a communication network.

14. An apparatus for acquiring and analyzing periodic information in vibration associated with a machine, the apparatus comprising:
a vibration sensor securely attached to the machine in a location providing a solid transmission path from a source of vibration within the machine to the vibration sensor, the vibration sensor for generating a vibration signal;
a data collector in communication with the vibration sensor, the data collector configured to receive and condition the vibration signal, the data collector comprising:
an analog-to-digital converter for converting the vibration signal to digital vibration data; and
memory for buffering the digital vibration data; and
a periodic information processor operable to receive the digital vibration data, the periodic information processor configured to execute operational instructions for processing the digital vibration data, the operational instructions comprising instructions which, when executed:
generate a vibration waveform based on the digital vibration data;
perform a Fast Fourier Transform on the vibration waveform to generate a vibration spectrum having amplitude values $Y_{VS}(n)$, where n=1 to N, and N is a number of frequency values;

perform an autocorrelation function on the a vibration waveform to generate an autocorrelation waveform;

perform a Fast Fourier Transform on the autocorrelation waveform to generate an autocorrelation spectrum having amplitude values $Y_{AS}(n)$, where n=1 to N, where N is the number of frequency values;

combine adjacent pairs of amplitude values $Y_{VS}(2n)$ and $Y_{VS}(2n-1)$ in the a vibration spectrum, according to $$Y_{MCVS}(n) = \sqrt{(Y_{VS}(2n-1))^2 + (Y_{VS}(2n))^2}; \text{ and}$$

combine the a vibration spectrum and the autocorrelation spectrum to generate a periodic information plot having amplitude values $Y_{PIP1}(n)$, according to $$Y_{PIP1}(n) = Y_{MCVS}(n) \times Y_{AS}(n), \text{ where } n=1 \text{ to } N.$$

wherein inclusion of the amplitude values $Y_{PIP1}(n)$ in the periodic information plot accentuates signal components that are pertinent to a diagnosis by an analyst while eliminating undesired non-periodic signal components, thereby improving visualization of pertinent signal components.

15. The apparatus of claim 14 wherein the periodic information processor is configured to execute operational instructions to generate a periodic information plot having amplitude values $Y_{PIP3}(n)$, according to If $Y_{PIP1}(n) > Y_{THR}$, $Y_{PIP3}(n) = Y_{PIP1}(n)$ If $Y_{PIP1}(n) \leq Y_{THR}$, $Y_{PIP3}(n) = 0$ where n=1 to N, and $Y_{THR}$ is a predetermined threshold value.

16. The apparatus of claim 14 wherein the periodic information processor is configured to execute operational instructions to perform an inverse Fast Fourier Transform on the periodic information plot to generate an information waveform.

17. The apparatus of claim 16 wherein the periodic information processor is configured to execute operational instructions to derive a circular information plot from the information waveform.

18. The apparatus of claim 14 wherein the periodic information processor is a component of the data collector.

19. The apparatus of claim 14 wherein the periodic information processor is a component of an analyst computer that is in communication with the data collector via a communication network.

20. An apparatus for acquiring and analyzing periodic information in vibration associated with a machine, the apparatus comprising:

a vibration sensor securely attached to the machine in a location providing a solid transmission path from a source of vibration within the machine to the vibration sensor, the vibration sensor for generating a vibration signal;

a data collector in communication with the vibration sensor, the data collector configured to receive and condition the vibration signal, the data collector comprising:

an analog-to-digital converter for converting the vibration signal to digital vibration data; and memory for buffering the digital vibration data; and a periodic information processor operable to receive the digital vibration data, the periodic information processor configured to execute operational instructions for processing the digital vibration data, the operational instructions comprising instructions which, when executed:

generate a vibration waveform based on the digital vibration data;

perform a Fast Fourier Transform on the vibration waveform to generate a vibration spectrum having amplitude values $Y_{VS}(n)$, where n=1 to M, and M is a number of frequency values;

perform an autocorrelation function on the vibration waveform to generate an autocorrelation waveform;

perform a Fast Fourier Transform on the autocorrelation waveform to generate an autocorrelation spectrum having amplitude values $Y_{AS}(n)$, where n=1 to N, where N is the number of frequency values;

combine adjacent pairs of amplitude values $Y_{VS}(2n)$ and $Y_{VS}(2n-1)$ in the vibration spectrum, according to $$Y_{MCVS}(n) = \sqrt{(Y_{VS}(2n-1))^2 + (Y_{VS}(2n))^2}; \text{ and}$$

generate a periodic information plot having amplitude values $Y_{PIP2}(n)$, according to If $Y_{AS}(n) > Y_{THR}$, $Y_{PIP2}(n) = Y_{MCVS}(n)$ If $Y_{AS}(n) \leq Y_{THR}$, $Y_{PIP2}(n) = 0$, where n=1 to N, and $Y_{THR}$ is a predetermined threshold value, wherein inclusion of only the amplitude values $Y_{PIP2}(n)$ in the periodic information plot accentuates signal components that are pertinent to a diagnosis by an analyst, while eliminating undesired non-periodic signal components, thereby improving visualization of pertinent signal components.

21. The apparatus of claim 20 wherein the periodic information processor is a component of the data collector.

22. The apparatus of claim 20 wherein the periodic information processor is a component of an analyst computer that is in communication with the data collector via a communication network.

23. An apparatus for acquiring and analyzing periodic information in vibration associated with a machine, the apparatus comprising:

a vibration sensor securely attached to the machine in a location providing a solid transmission path from a source of vibration within the machine to the vibration sensor, the vibration sensor for generating a vibration signal;

a data collector in communication with the vibration sensor, the data collector configured to receive and condition the vibration signal, the data collector comprising:

an analog-to-digital converter for converting the vibration signal to digital vibration data; and memory for buffering the digital vibration data; and a periodic information processor operable to receive the digital vibration data, the periodic information processor configured to execute operational instructions for processing the digital vibration data, the operational instructions comprising instructions which, when executed:

generate a vibration waveform based on the digital vibration data;

perform a Fast Fourier Transform on the digital vibration data to generate a vibration spectrum having amplitude values $Y_{VS}(n)$, where n=1 to N, where N is a number of frequency values;

combine adjacent pairs of amplitude values $Y_{VS}(2n)$ and $Y_{VS}(2n-1)$ in the vibration spectrum, according to $$Y_{MCVS}(n) = \sqrt{(Y_{VS}(2n-1))^2 + (Y_{VS}(2n))^2};$$

perform an autocorrelation function on the vibration waveform to generate an autocorrelation waveform;
perform a Fast Fourier Transform on the autocorrelation waveform to generate an autocorrelation spectrum having amplitude values $Y_{AS}(n)$, where n=1 to N, where N is the number of frequency values; and
combine the vibration spectrum and the autocorrelation spectrum to generate a periodicity map having coordinate values $X_{PM}(n)$ and $Y_{PM}(n)$ determined according to $$X_{PM}(n)=Y_{MCVS}(n)$$

$$Y_{PM}(n)=Y_{AS}(n)$$

for n=1 to N.

24. The apparatus of claim 23 wherein the periodic information processor is a component of the data collector.

25. The apparatus of claim 23 wherein the periodic information processor is a component of an analyst computer that is in communication with the data collector via a communication network.

26. An apparatus for acquiring and analyzing periodic information in vibration associated with a machine, the apparatus comprising:
a vibration sensor securely attached to the machine in a location providing a solid transmission path from a source of vibration within the machine to the vibration sensor, the vibration sensor for generating a vibration signal;
a data collector in communication with the vibration sensor, the data collector configured to receive and condition the vibration signal, the data collector comprising:
an analog-to-digital converter for converting the vibration signal to digital vibration data; and
memory for buffering the digital vibration data; and
a periodic information processor operable to receive the digital vibration data, the periodic information processor configured to execute operational instructions for processing the digital vibration data, the operational instructions comprising instructions which, when executed:
generate a vibration waveform based on the digital vibration data;
perform an autocorrelation function on the vibration waveform to generate an autocorrelation waveform;
perform a Fast Fourier Transform on the autocorrelation waveform to generate an autocorrelation spectrum having amplitude values $Y_{AS}(n)$, where n=1 to N;
generate a non-periodic information plot having amplitude values $Y_{NPIP}(n)$, according to If $Y_{AS}(n) < Y_{THR}$, $Y_{NPIP}(n) = Y_{AS}(n)$ If $Y_{AS}(n) \geq Y_{THR}$, $Y_{NPIP}(n) = 0$, where n=1 to N, and $Y_{THR}$ is a predetermined threshold value,
wherein inclusion of only the amplitude values $Y_{NPIP}(n)$ in the non-periodic information plot accentuates signal components that are pertinent to a diagnosis by an analyst, while eliminating undesired non-periodic signal components, thereby improving visualization of pertinent signal components.

27. The apparatus of claim 26 wherein the periodic information processor is a component of the data collector.

28. The apparatus of claim 26 wherein the periodic information processor is a component of an analyst computer that is in communication with the data collector via a communication network.

29. An apparatus for acquiring and analyzing periodic information in vibration associated with a machine, the apparatus comprising:
a vibration sensor securely attached to the machine in a location providing a solid transmission path from a source of vibration within the machine to the vibration sensor, the vibration sensor for generating a vibration signal;
a tachometer sensor configured to be attached to the machine and generate a turning speed;
a data collector in communication with the vibration sensor and the tachometer sensor, the data collector configured to receive and condition the vibration signal and the turning speed, the data collector comprising:
an analog-to-digital converter for converting the vibration signal to digital vibration data; and
memory for buffering the digital vibration data; and
a periodic information processor operable to receive the digital vibration data, the periodic information processor configured to execute operational instructions for processing the digital vibration data, the operational instructions comprising instructions which, when executed:
generate a vibration waveform based on the digital vibration data;
determine a maximum peak amplitude of the vibration waveform;
perform an autocorrelation function on the vibration waveform to generate an autocorrelation waveform;
determine a periodic signal parameter value based at least in part on the autocorrelation waveform, where the periodic signal parameter value comprises a single real number indicative of a level of periodic information in the vibration waveform;
calculate or receive a fault limit level; and
calculate one or more severity values based on the maximum peak amplitude and the fault limit level.

30. The apparatus of claim 29 wherein the periodic information processor is a component of the data collector.

31. The apparatus of claim 29 wherein the periodic information processor is a component of an analyst computer that is in communication with the data collector via a communication network.

32. The apparatus of claim 29 wherein the vibration waveform is a PeakVue waveform.

33. The apparatus of claim 29 wherein, if the periodic signal parameter value is greater than 0.1 or % Periodic Energy is greater than a predetermined percentage, and machine speed is unknown, the periodic information processor calculates a Bearing Fault Severity (BFS) value according to:

$$BFS = \text{Normalized Severity} \times \% \text{ Periodic Energy,}$$

where $$\text{Normalized Severity} = \frac{\text{MaxPeak}}{2 \times \text{Fault Limit}} \times x$$

and $$\% \text{ Periodic Energy} = \sqrt{\text{MaxPeak(after first 3\% of autocorrelation wave form)}}.$$

34. The apparatus of claim 29 wherein, if the periodic signal parameter value is greater than 0.1 or % Periodic Energy is greater than a predetermined percentage, and machine speed is known, the periodic information processor calculates a Bearing Fault Severity (BFS) value according to:

$$BFS = \text{Normalized severity} \times \left[\left(\frac{(\text{energy of the located nonsychronous peaks})^2}{(\text{total energy of the associated } PeakVue \text{ spectrum})^2}\right)\right]$$

where $$\text{Normalized Severity} = \frac{\text{MaxPeak}}{2 \times \text{Fault Limit}} \times x.$$

wherein x is a normalization factor.

35. The apparatus of claim 29 further comprising the periodic information processor configured to execute operational instructions to calculate an alert limit level based on the turning speed, wherein if the periodic signal parameter value is less than 0.1 or % Periodic Energy is less than a predetermined percentage, and the maximum peak amplitude of the vibration waveform is greater than the alert limit level, the periodic information processor calculates a Lubrication Severity (LS) value according to:

$$LS = \frac{\text{MaxPeak}}{2 \times \text{Fault Limit}} \times x \times \% \ NPE,$$

wherein Percent Non-Periodic Energy (% NPE) is a function of Percent Periodic Energy (% Periodic Energy), and Percent Periodic Energy is calculated from the autocorrelation waveform according to:

$$\% \text{ Periodic Energy} = \sqrt{\text{MaxPeak}(\text{after first 3\% of autocorrelation wave form})}.$$

36. The apparatus of claim 29 wherein, if the periodic signal parameter value is greater than 0.1 or % Periodic Energy is greater than a predetermined percentage, the periodic information processor executes operational instructions to calculate a Gearbox Fault Severity (GFS) value according to:

$$GFS = \text{Normalized Severity} \times \left[\left(\frac{(\text{energy of the located synchronous peaks})^2}{(\text{total energy of the associated } PeakVue \text{ spectrum})^2}\right)\right]$$

wherein

Normalized Severity = General Severity $\times x$ and

General Severity = MaxPeak / (2 × Fault Limit)

and $x$ is a normalization factor.

* * * * *